United States Patent
Lash et al.

(10) Patent No.: US 10,456,079 B1
(45) Date of Patent: *Oct. 29, 2019

(54) DETECTING AND AVOIDING BLOOD VESSELS

(71) Applicant: ViOptix, Inc., Newark, CA (US)

(72) Inventors: Robert E. Lash, Redwood City, CA (US); Jimmy Jian-min Mao, Redwood City, CA (US)

(73) Assignee: ViOptix, Inc., Newark, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/209,945

(22) Filed: Dec. 4, 2018

Related U.S. Application Data

(63) Continuation of application No. 15/638,323, filed on Jun. 29, 2017, now Pat. No. 10,149,650, which is a
(Continued)

(51) Int. Cl.
*A61B 5/00* (2006.01)
*A61B 17/34* (2006.01)
(Continued)

(52) U.S. Cl.
CPC .......... *A61B 5/489* (2013.01); *A61B 1/00013* (2013.01); *A61B 5/00* (2013.01);
(Continued)

(58) Field of Classification Search
CPC ... A61B 17/3403; A61B 1/00013; A61B 5/00; A61B 5/0084; A61B 5/02416;
(Continued)

(56) References Cited

U.S. PATENT DOCUMENTS 2,198,319 A  10/1938 Silverman
4,609,370 A   9/1986 Morrison
(Continued)

OTHER PUBLICATIONS

Benaron, David et al., "Design of a Visibile-Light Spectroscopy Clinical Tissue Oximeter", Journal of Biomedical Optics, vol. 1014, Jul./Aug. 2005, pp. 044005-1-044005-9.
(Continued)

*Primary Examiner* — Ruth S Smith
(74) *Attorney, Agent, or Firm* — Aka Chan LLP

(57) ABSTRACT

A method differentiates a blood vessel from a nonvascular tissue during a minimally invasive surgery using a device. A device may be any penetration sensor device, such as a dilator sensor device, a hollow needle sensor device, or a trocar sensor device, which penetrates the skin and subcutaneous layers to reach a target location inside the body. The penetration sensor device includes a sensor probe which can make optical measurements to determine various parameters of the tissue at the tip of the sensor probe. These parameters may include an optical signal level returned from tissue contacting the tip of the sensor probe, an oxygen saturation level of the tissue, a total hemoglobin concentration, a blood flow, and a pulse. Based on these parameters, the presence or absence of a blood vessel at the tip of the penetration sensor device can be determined while the device travels towards the target location for surgery.

36 Claims, 11 Drawing Sheets

Related U.S. Application Data continuation of application No. 15/269,929, filed on Sep. 19, 2016, now Pat. No. 9,693,729, which is a continuation of application No. 12/568,470, filed on Sep. 28, 2009, now Pat. No. 9,445,766.

(60) Provisional application No. 61/224,008, filed on Jul. 8, 2009.

(51) Int. Cl.
    *A61B 5/06* (2006.01)
    *A61M 29/02* (2006.01)
    *A61B 5/1459* (2006.01)
    *A61B 5/026* (2006.01)
    *A61B 5/024* (2006.01)
    *A61B 5/1455* (2006.01)
    *A61M 29/00* (2006.01)
    *A61B 1/00* (2006.01)

(52) U.S. Cl.
    CPC .......... *A61B 5/0084* (2013.01); *A61B 5/0261* (2013.01); *A61B 5/02416* (2013.01); *A61B 5/065* (2013.01); *A61B 5/1459* (2013.01); *A61B 5/14551* (2013.01); *A61B 5/6847* (2013.01); *A61B 5/6848* (2013.01); *A61B 17/3403* (2013.01); *A61M 29/00* (2013.01); *A61M 29/02* (2013.01)

(58) Field of Classification Search
    CPC ... A61B 5/0261; A61B 5/065; A61B 5/14551; A61B 5/1459; A61B 5/489; A61B 5/6847; A61B 5/6848; A61M 29/00; A61M 29/02
    See application file for complete search history.

(56) References Cited

U.S. PATENT DOCUMENTS

| | | |
|---|---|---|
| 5,084,022 A | 1/1992 | Claude |
| 5,168,873 A | 12/1992 | Seifert et al. |
| 5,183,464 A | 2/1993 | Dubrul et al. |
| 5,460,182 A | 10/1995 | Goodman et al. |
| 5,480,388 A | 1/1996 | Zadini et al. |
| 5,693,043 A | 12/1997 | Kittrell et al. |
| 5,746,210 A | 5/1998 | Benaron et al. |
| 5,752,519 A | 5/1998 | Benaron et al. |
| 5,762,609 A | 6/1998 | Benaron et al. |
| 5,769,076 A | 6/1998 | Maekawa et al. |
| RE36,434 E | 12/1999 | Hamlin et al. |
| 6,078,833 A | 6/2000 | Klueber |
| 6,246,901 B1 | 6/2001 | Benaron |
| 6,280,702 B1 | 8/2001 | Carter et al. |
| 6,516,209 B2 | 2/2003 | Cheng et al. |
| 6,517,530 B1 | 2/2003 | Kleven |
| 6,587,703 B2 | 7/2003 | Cheng et al. |
| 6,594,518 B1 | 7/2003 | Benaron et al. |
| 6,597,931 B1 | 7/2003 | Cheng et al. |
| 6,626,902 B1 | 9/2003 | Kucharczyk et al. |
| 6,718,196 B1 | 4/2004 | Mah et al. |
| 6,735,458 B2 | 5/2004 | Cheng et al. |
| 6,801,648 B2 | 10/2004 | Cheng |
| 7,207,949 B2 | 4/2007 | Miles et al. |
| 7,247,142 B1 | 7/2007 | Elmandjra et al. |
| 7,302,287 B2 | 11/2007 | Gandjbakhche et al. |
| 7,331,943 B2 | 2/2008 | Mascitelli et al. |
| 7,355,688 B2 | 4/2008 | Lash et al. |
| 7,488,292 B2 | 2/2009 | Kdachi |
| 7,522,953 B2 | 4/2009 | Kaula et al. |
| 7,525,647 B2 | 4/2009 | Lash et al. |
| 7,538,865 B2 | 5/2009 | Lash et al. |
| 7,727,226 B2 | 6/2010 | Chang et al. |
| 9,114,226 B1 | 8/2015 | Lash et al. |
| 9,445,766 B1 | 9/2016 | Lash et al. |
| 9,693,729 B1 | 7/2017 | Lash et al. |
| 10,149,650 B1 * | 12/2018 | Lash ................... A61M 29/00 |
| 2004/0127776 A1 | 7/2004 | Walker et al. |
| 2005/0065401 A1 | 3/2005 | Saadat et al. |
| 2005/0149035 A1 | 7/2005 | Pimenta et al. |
| 2006/0004286 A1 | 1/2006 | Chang et al. |
| 2007/0038126 A1 | 2/2007 | Pyle et al. |
| 2008/0081975 A1 | 4/2008 | Agashe et al. |
| 2008/0106792 A1 | 5/2008 | Lash et al. |
| 2008/0108886 A1 | 5/2008 | Lash et al. |
| 2008/0319290 A1 | 12/2008 | Mao et al. |
| 2009/0024089 A1 | 1/2009 | Levine et al. |
| 2009/0234225 A1 | 9/2009 | Martin et al. |

OTHER PUBLICATIONS

Hirano, Yasumitso et al., "Near-Infrared Spectroscopy for Assessment of Tissue Oxygen Saturation of Transplanted Jejunal Autografts in Cervical Esophageal Reconstruction", Surgery Today, 2005, vol. 35, pp. 67-72.

"Intraoperative Assessment of Microperfusion with Visible Light Spectroscopy in Colorectal Anastomosis", Diagnostic Optical Spectroscopy in Biomedicine IV, Proc. of SPIE-OSA, vol. 6628, 2007, pp. 662816-1-662816-8.

Musgrove, Cameron et al., "Computational Aspects of Endoscopic (Trans-rectal) Near-infrared Optical Tomography: Initial Investigations", Optical Tomography and Spectroscopy of Tissue VII, Proc. of SPIE, vol. 6434, 2007, pp. 643409-1-643409-10.

Rosenthal, Lawrence et al., "Internal Ischemia", http://www.gi.org/patients/gihealth/ischemia.asp, American College of Gastroenterology, 2006, 3 pages, (viewed Mar. 10, 2009).

Williams, Julian, "Encoscope and Laser Treatment", http://julzwilliams.com/files/physics/ endolaser/partsofendoscope.html, 2008, 1 page, (viewed Mar. 10, 2009).

R. Bonner et al., "Model for laser Doppler measurements of blood flow in tissue", Applied Optics, vol. 20, No. 12, 2097-2107 (1981).

P. Elter et al., "Noninvasive, real time laser Doppler flowmetry in perfusion regions and larger vessels", SPIE proceesing, vol. 3570, 244-254 (1998).

* cited by examiner

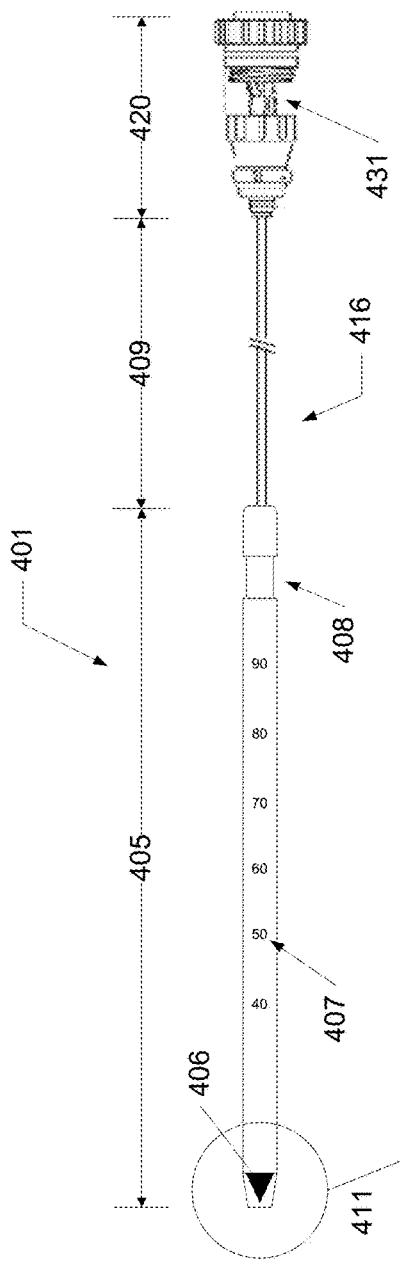
Figure 4A
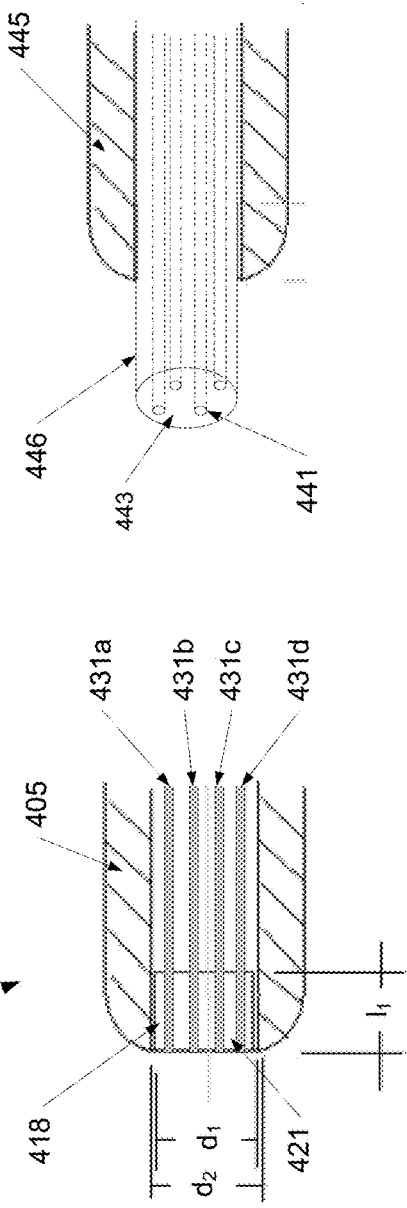
Figure 4B
Figure 4C

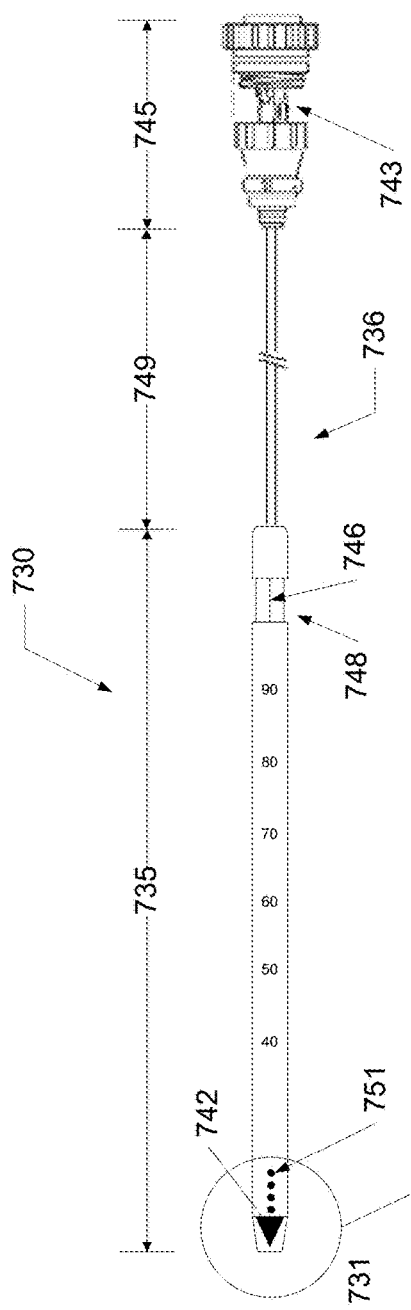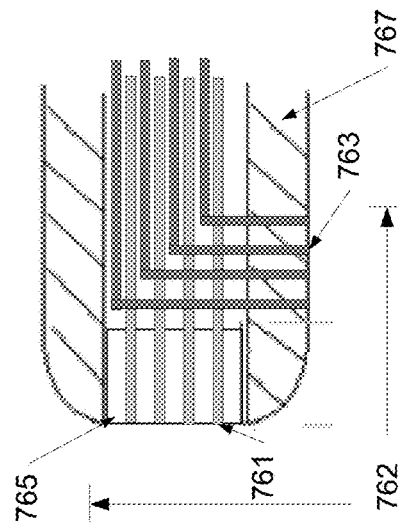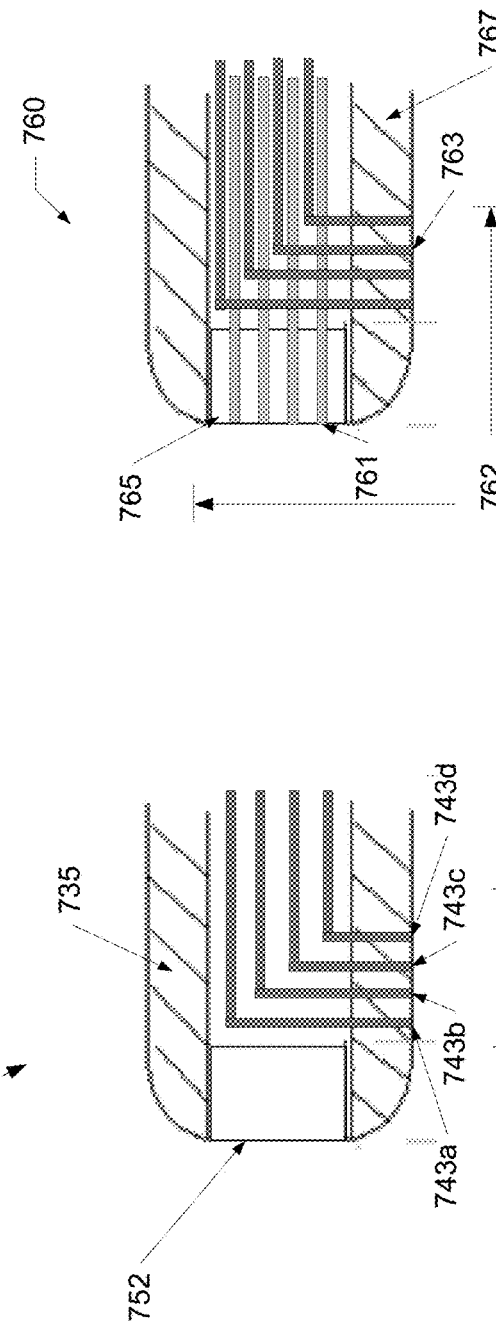
Figure 7C
Figure 7E
Figure 7D

DETECTING AND AVOIDING BLOOD VESSELS

CROSS-REFERENCE TO RELATED APPLICATIONS

This patent application is a continuation of U.S. patent application Ser. No. 15/638,323, filed Jun. 29, 2017, issued as U.S. Pat. No. 10,149,650 on Dec. 11, 2018, which is a continuation of U.S. patent application Ser. No. 15/269,929, filed Sep. 19, 2016, issued as U.S. Pat. No. 9,693,729 on Jul. 4, 2017, which is a continuation of U.S. patent application Ser. No. 12/568,470, filed Sep. 28, 2009, issued as U.S. Pat. No. 9,445,766 on Sep. 20, 2016, which claims the benefit of U.S. patent application 61/224,008, filed Jul. 8, 2009. These applications are incorporated by reference along with all other references cited in this application.

BACKGROUND OF THE INVENTION

Minimally invasive or minimal access surgeries involve a modern technique in which operations inside the body are performed through small incisions. This technique is now being favored by surgeons over traditional open surgeries which require large incisions to gain access to the target surgical site. In addition to requiring larger incisions, traditional open surgeries require displacing a large amount of peripheral tissue to gain access to the target surgical site as well as a greater volume of blood loss for the patient. Thus, after traditional open surgeries, patients have to deal with a longer recuperation time, a greater degree of pain and scar. Minimally invasive or minimal access surgeries reduce these undesirable results of traditional open surgeries.

In minimally invasive surgical procedures, access to organs, tissue, and cavities inside the body is usually provided by inserting a cannula or other instruments through a small access hole. The initial access is usually created by piercing the skin and subcutaneous layers with a needle, a trocar, or both. Sometimes a series of dilators with increasingly larger diameters is used to enlarge a working channel for minimally invasive surgeries.

While minimally invasive surgeries have many advantages over traditional open surgeries, injuries to internal organs, tissues, blood vessels and nerves may occur during the initial step of blindly introducing a needle, trocar, dilator, or other instruments into the body. In fact, a vascular injury is a major cause of death from laparoscopy. The reason for a vascular injury is proximity of the abdominal wall to the retroperitoneal blood vessels, such as distal aorta and iliac artery and vein.

Thus, there is a need to improve minimally invasive or minimal access surgeries when an initial instrument, such as a needle, trocar, or dilator, is introduced into the body cavity. It would be desirable to have a monitoring system which allows a surgeon to determine if there are any vital organs or tissues, such as blood vessels or nerves, near the distal end of the initial instrument so that the damage to the organs and tissues can be avoided or minimized.

Embodiments of the invention meet this and other needs.

BRIEF SUMMARY OF THE INVENTION

The present invention relates methods for differentiating a blood vessel from a nonvascular tissue during a minimally invasive or minimal access surgery. A penetration sensor device which has optical fibers is inserted into a patient's body during the surgery. A sensor unit at the tip of the penetration sensor device transmits light into tissue and light reflected and scattered from the tissue is transmitted to a monitoring console or a system unit. The system unit can determine whether a blood vessel is present near the tip of the penetration sensor device. A surgeon can use this information to avoid rupturing the blood vessel when moving the penetration sensor device towards a target surgical site.

According to one aspect of the invention, a method relates to differentiating a blood vessel from a nonvascular tissue inside a patient's body cavity during a surgical procedure. The method includes transmitting a first light signal through one or more optical fibers in a penetration sensor device into a tissue. A second light signal reflected from the tissue is then received through the one or more optical fibers in the penetration sensor device. Then an indicator for presence of a blood vessel at or nearby a tip of the penetration sensor device can be determined based on information from the first light signal and the second light signal. If the indicator for presence of a blood vessel is greater than a threshold, then the tissue at the tip of the penetration sensor device is identified as a blood vessel.

In embodiments of the invention, a penetration sensor device generally includes a penetration instrument having a tubular body with a lumen along a longitudinal axis of the tubular body, and a sensor probe, coupled to the penetration instrument. The sensor probe includes a sensor unit, at a tip of the sensor probe, having sensor openings, one or more optical fibers which are coupled to the sensor openings in the sensor unit, and a connector which includes proximal ends of the optical fibers and is configured to couple the penetration sensor device to a system unit.

In one embodiment, the indicator for presence of a blood vessel is determined based on one or combinations of parameters which include a signal level of the second light, a total hemoglobin concentration, an oxygen saturation level, a blood flow, and a pulse.

In another embodiment, a dilator sensor device is used as a penetration sensor device in the method to differentiate a blood vessel from a nonvascular tissue.

In yet another embodiment, the method further includes alerting a user if the indicator for presence of a blood vessel indicates that there is a blood vessel at or nearby the tip of the sensor probe.

In yet another embodiment, the method further includes instructing a user to advance the penetration sensor device towards a target location if the indicator for presence of a blood vessel indicates that the tip of the sensor probe is touching a nonvascular tissue.

In yet another embodiment, the method further includes rerouting the penetration sensor device into a different direction if the indicator for presence of a blood vessel indicates that the tip of the sensor probe is nearby or touching a blood vessel so that the blood vessel is not punctured by the penetration sensor device.

In yet another embodiment, the method includes using a penetration sensor device which may be a dilator sensor device, a needle sensor device, or a trocar sensor device.

In yet another embodiment, the method includes using a penetration sensor device with sensor openings which are located at the tip of the penetration instrument and the distal ends of the optical fibers are aligned along a longitudinal axis of the penetration sensor device.

In yet another embodiment, the method includes using a penetration sensor device with sensor openings which are located on a side wall of the penetration instrument near a tip of the penetration instrument and the distal ends of the optical fibers are radially aligned with respect to the penetration sensor device.

In yet another embodiment, the method includes using a penetration sensor device with at least two sets of sensor openings and two sets of optical fibers, where a first set of sensor openings are located at the tip of the penetration instrument with a first set of optical fibers coupled to the first set of sensor openings and where a second set of sensor openings are located on a side wall of the penetration instrument with a second set of optical fibers coupled to the second set of sensor openings.

In yet another embodiment, the method includes using a penetration sensor device with at least one source fiber and at least one detector fiber, where the sensor openings in the sensor unit of the penetration sensor device are separated by a distance of at least 1 millimeter.

In yet another embodiment, the method includes using a penetration sensor device with two source fibers and two detector fibers, where the sensor openings in the sensor unit of the penetration sensor device are separated by a distance of at least 1 millimeter.

Another aspect of the invention relates to a method of accessing a spinal target site. The method includes inserting a guider, such as a surgeon's finger, through a first incision into a retroperitoneal space. A distal end of a dilator sensor device is inserted through a second incision into tissue in a substantially lateral direction towards the spinal target site. Using the guider, the distal tip of the dilator is directed through the retroperitoneal space. The dilator sensor device is advanced in a substantially lateral direction toward the spinal target site while using a monitoring system for a blood vessel to detect the blood vessel proximal to the dilator sensor device.

In one embodiment, the method includes detecting blood vessels in front of the tip of the dilator sensor device.

In another embodiment, the method further includes detecting nerves proximal to the dilator sensor device.

In yet another embodiment, the method further includes identifying the tissue as the blood vessel if the blood vessel has a diameter greater than about 3 millimeters.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 4A shows a dilator sensor device where a connector is disassembled to show optical fibers inside the connector.

FIG. 4B shows a longitudinal cross sectional view of the tip of a dilator sensor device shown in FIG. 4A containing optical fibers, forming a forward looking sensor array.

FIG. 4C shows a tip of another dilator sensor device.

FIG. 7C shows a dilator sensor device with sensor openings on a side wall of a dilator.

FIG. 7D shows a longitudinal cross sectional view of the tip of a dilator sensor device shown in FIG. 7C containing optical fibers, forming a side looking sensor array.

FIG. 7E shows another dilator sensor device with both a forward looking sensor array and a side looking sensor array.

DETAILED DESCRIPTION OF THE INVENTION

Figure 1:
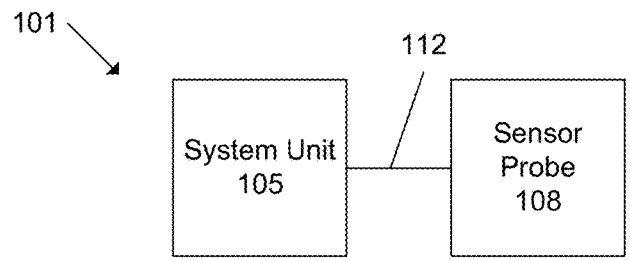
FIG. 1 shows a block diagram of a system for obtaining optical measurements of tissue in a patient.

During a minimally invasive or minimal access surgery, a penetration instrument such as a needle, a trocar, or a dilator is often the first instrument that is blindly inserted into a body. It is often one of the most dangerous steps during a minimally invasive or minimal access surgery because of the blind nature of this surgical step. These penetration instruments can puncture important organs or tissues such as blood vessels or nerves. While intraoperative techniques such as X-ray, ultrasound imaging, or other visual aids can provide some information, the information is limited and is not sensitive enough to detect the presence of blood vessels or nerves at the tip of the penetration instrument.

The present invention provides various penetration sensor devices and systems that allow a safe introduction of a penetration instrument into a patient's body during a minimally invasive surgery. The penetration sensor devices and systems in accordance with the present invention include a sensor probe which is coupled to a penetration instrument. In this application, the penetration instrument refers to any suitable instrument that is introduced into a body by penetrating through the skin and subcutaneous layers of the patient's body. Examples of penetration instruments include a hollow needle instrument, a trocar, and a dilator. A sensor probe is typically placed inside a lumen of these instruments.

In a penetration sensor device and system, a sensor probe is configured to transmit a light signal into a tissue as the penetration sensor device is penetrating and advancing towards a target surgical site inside the patient's body. The sensor probe also transmits a light signal that is reflected from the tissue back to a monitoring console. Based on the initial light signal and returned light signal, the monitoring console can calculate one or more parameters of a tissue at or proximal to the tip of the device (e.g., the tissue contacting the tip of the sensor probe and underlying tissue). These parameters include a signal level of the returned light, a total hemoglobin concentration, an oxygen saturation level, a blood flow, and a pulse.

Based on one or combinations of these parameters, the monitoring console can determine an indicator or index for presence of a blood vessel at or proximal to the tip of the sensor probe. The indicator or index provides whether blood vessels or nonvascular tissue are contacting or in front of the tip of the sensor probe. A blood vessel and nonvascular tissue will have result in different optical measurements and parameters.

For example, a blood vessel has a relatively high total hemoglobin concentration and a blood flow compared to a nonvascular tissue. Furthermore, a blood vessel which has abundant hemoglobins will absorb more infrared or visible red light than nonvascular tissue. A strong pulse is also present in arteries but not in nonvascular tissue. Based on these and other differences, the penetration sensor devices and systems in accordance with the present invention can be used to safely insert the device into a body without puncturing blood vessels.

Embodiments of the invention can be used in a wide variety of applications. One application is in a minimally invasive anterior lumbar interbody fusion procedure. During this procedure, a degenerated disk is replaced with an implant through a small single incision. A dilator is typically introduced, via retroperitoneal approach, as one of the first instruments into the body towards a lumbar region of the spine. In the pathway towards the lumbar region, a dilator needs to avoid two major blood vessels (i.e., iliac artery and vein) when passing through the psoas muscle region. Rather than using a traditional dilator, a dilator sensor device in accordance with the present invention can be used. The dilator sensor device can monitor the presence of major blood vessels, such as iliac artery and vein, as it is advanced through the psoas muscle region. Thus, puncturing these blood vessels can be avoided during the surgical procedure.

The penetration sensor devices and systems in accordance with the present invention can also be used in other laparoscopic surgeries. Laparoscopic surgery includes operations within the abdominal or pelvic cavities through small incisions. As an initial step, the abdomen is usually insufflated with carbon dioxide gas with an insufflation needle. In addition, a penetration instrument such as a trocar is inserted into the abdomen to create an operative corridor. The insufflation needle and trocar are often blindly inserted into the abdomen and can puncture a blood vessel which can be fatal to the patient. The penetration devices and systems in accordance with the present invention can be used in these procedures to minimize the risk of an instrument puncturing a blood vessel while it is being introduced into the body cavity.

In this application, a blood vessel refers to a tube or channel that blood is carried through in order to reach the various tissues throughout the body. Blood flow in the vessels of the human body generally goes through aorta, artery, arteriole, capillary, venule, and vein. In one embodiment, it is desired that the monitoring system in accordance with the present invention is sensitive enough to avoid all types of blood vessels. In another embodiment, it is desired that the monitoring system is adjusted to avoid major arteries, veins and aorta. In yet another embodiment, it is desired that the monitoring system is adjusted to avoid aorta, arteries, veins, arterioles, and venules.

In embodiments of the invention, the monitoring system and its sensor probe are designed such that a penetration sensor device can avoid puncturing or damaging a blood vessel with a diameter greater than about 1, 2, 3, 4, or 5 millimeters. In a specific implementation, a penetration sensor device is configured such that it can avoid puncturing or damaging a blood vessel with a diameter greater than about 3 millimeters. For example, in anterior lumbar interbody fusion (ALIF) spine surgery, a penetration sensor device in accordance with the present invention can be designed to detect the iliac artery and vein which have a diameter between about 5 millimeters to about 15 millimeters.

Examples of embodiments of the invention are illustrated using figures and are described below. The figures described herein are used to illustrate embodiments of the invention, and are not in any way intended to be restrictive of the broad invention. Embodiments of the invention are not limited to the specific arrangements and constructions shown and described. For example, features shown in one figure can be combined with features shown in another figure.

FIG. 1 shows a system 101 for measuring various parameters of a tissue in a patient. The parameters of the tissue measured by the system may include an oxygen saturation level, a total hemoglobin concentration, a blood flow, a pulse, and a signal level of light reflected from the tissue. The system includes a system unit 105 and a sensor probe 108, which is connected to the system unit via a wired connection 112. Connection 112 may be an electrical, optical, or another wired connection including any number of wires (e.g., one, two, three, four, five, six, or more wires or optical fibers), or any combination of these or other types of connections. In other implementations of the invention, however, connection 112 may be wireless such as via a radio frequency (RF) or infrared communication.

Typically, the system is used by placing the sensor probe in contact or close proximity to tissue (e.g., skin or internal organ or tissue) at a site where tissue parameter measurements are desired. The system unit causes an input signal to be emitted by the sensor probe into the tissue (e.g., human tissue). There may be multiple input signals, and these signals may have varying or different wavelengths. The input signal is transmitted into or through the tissue.

Then, after transmission through or reflection off the tissue, the signal is received at the sensor probe. This received signal is received and analyzed by the system unit. Based on the received signal, the system unit determines various parameters of the tissue—an oxygen saturation level, a total hemoglobin concentration, a blood flow, a pulse, a signal level of light reflected from the tissue. One or any combinations of these parameters can be displayed on a display screen of the system unit.

In an implementation, the system is a tissue oximeter, which can measure oxygen saturation and hemoglobin concentration, without requiring a pulse or heart beat. A tissue oximeter of the invention is applicable to many areas of medicine and surgery including plastic surgery and spinal surgery. The tissue oximeter can make oxygen saturation and hemoglobin concentration measurements of tissue where there is no pulse; such tissue, for example, may have been separated from the body (e.g., a flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbance of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. These patents are assigned to the same assignee as this patent application and are incorporated by reference.

In an implementation, the system is a laser Doppler flow meter, which can measure a blood flow, a pulse rate, or both in the tissue. In principle, this technique involves directing a laser beam (e.g., through optical fibers) onto a part of the tissue and receiving, with the aid of an appropriate detector, part of the light scattered and reflected back by that part of the tissue that is irradiated by the laser beam. When light hits moving blood cells, the light undergoes a change in wavelength, which may be referred to as a Doppler shift, while light hitting nonmoving tissue is unchanged. The magnitude and frequency distribution of these changes in wavelength are directly related to the number and velocity of blood cells but unrelated to their direction of movement. This information is captured by returning optical fibers in the sensor probe, converted into an electrical signal and analyzed.

In an implementation, the system is both a tissue oximeter and laser Doppler flow meter. Therefore, the system can simultaneously determine multiple parameters of a tissue, which may include a signal level of returned light, oxygen saturation level, total hemoglobin concentration, blood flow, pulse rate, and others.

Figure 2:
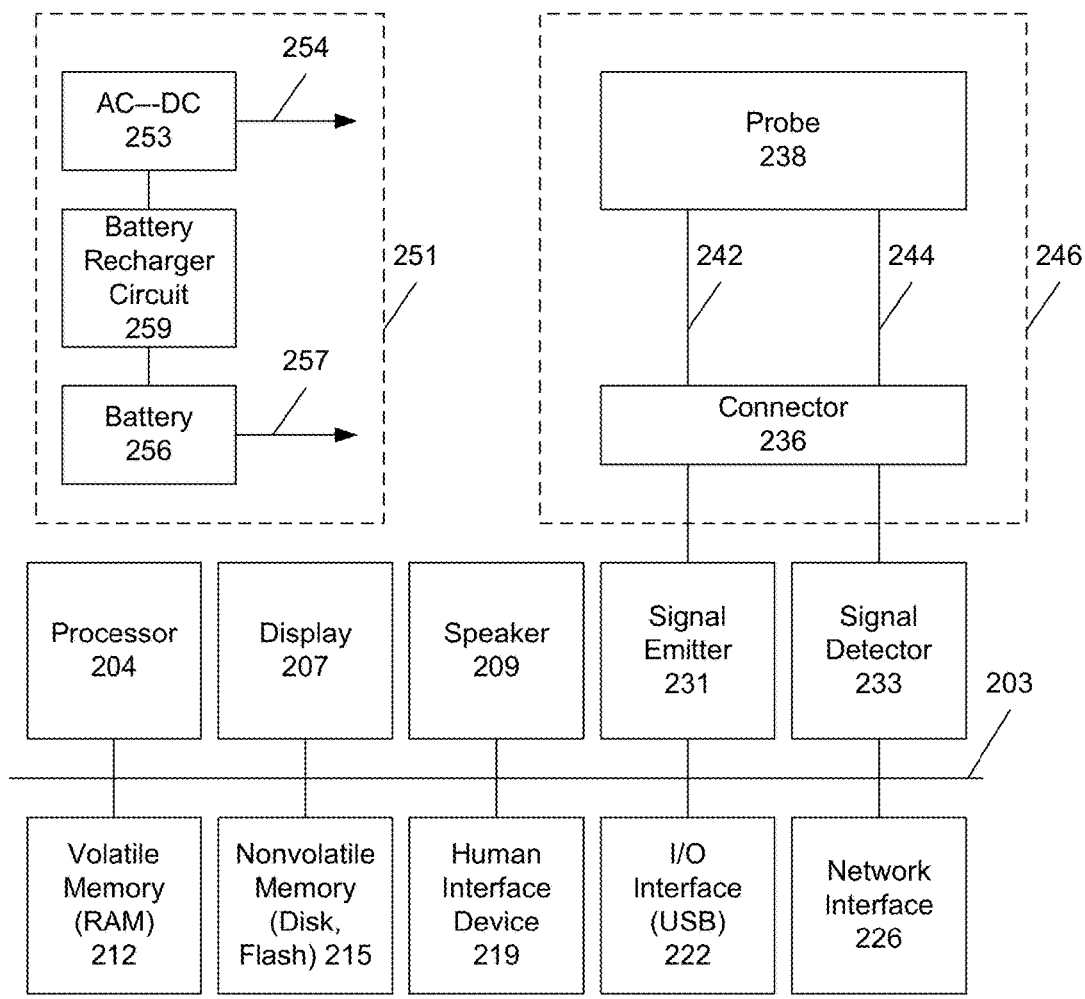
FIG. 2 shows a more detailed block diagram of a specific implementation of the system of FIG. 1.

FIG. 2 shows greater detail of a specific implementation of the system of FIG. 1. The system includes a processor 204, display 207, speaker 209, signal emitter 231, signal detector 233, volatile memory 212, nonvolatile memory 215, human interface device or HID 219, I/O interface 222, and network interface 226. These components are housed within a system unit enclosure. Different implementations of the system may include any number of the components described, in any combination or configuration, and may also include other components not shown.

The components are linked together using a bus 203, which represents the system bus architecture of the system. Although this figure shows one bus that connects to each component, the busing is illustrative of any interconnection scheme serving to link the subsystems. For example, speaker 209 could be connected to the other subsystems through a port or have an internal direct connection to processor 204.

A sensor probe 246 of the system includes a probe 238 and connector 236. The probe is connected to the connector using wires 242 and 244. The connector removably connects the probe and its wires to the signal emitter and signal detectors in the system unit. There is one cable or set of cables 242 to connect to the signal emitter, and one cable or set of cables 244 to connect to the signal detector. In an implementation the cables are fiber optic cables, but in other implementations, the cables are electrical wires. In yet another implementation, the cables include both fiber optic cables and electrical wires.

Signal emitter 231 is a light source that emits light at one or more specific wavelengths. In a specific implementation, two wavelengths of light (e.g., 690 nanometers and 830 nanometers) are used. In other implementations, other wavelengths of light may be used. The signal emitter is typically implemented using a laser diode or light emitting diode (LED). Signal detector 233 is typically a photodetector capable of detecting the light at the wavelengths produced by the signal emitter.

Connector 236 may have a locking feature; e.g., insert connector, and then twist or screw to lock. If so, the connector is more securely held to the system unit and it will need to be unlocked before it can be removed. This will help prevent accidental removal of the probe.

The connector may also have a first keying feature, so that the connector can only be inserted into a connector receptacle of the system unit in one or more specific orientations. This will ensure that proper connections are made.

The connector may also have a second keying feature that provides an indication to the system unit which type of probe is attached. The system unit may handle making measurements for a number of different types of probes. When a probe is inserted, the system uses the second keying feature to determine which type of probe is connected to the system. Then the system can perform the appropriate functions, use the proper algorithms, or otherwise make adjustments in its operation for the specific probe type.

For example, when the system detects a probe with two optical fiber ends at its scanning surface is connected, the system uses probe algorithms and operation specific for the two optical fiber probe. When the system detects that a probe with four optical fiber ends at its scanning surface is connected, the system uses probe algorithms and operation specific for the four optical fiber probe. When the system detects that a probe in a dilator is connected, the system uses dilator probe algorithms and operation. When the system detects that a probe in a hollow needle is connected, the system uses needle probe algorithms and operation. A system can handle any number of different types of probes. There may be different probes for measuring different parts of the body, or different sizes or versions of a probe for measuring a part of the body.

With the second keying feature, the system will be able to distinguish between the different probes. The second keying feature can use any type of coding system to represent each probe including binary coding. For example, for a probe, there are four second keying inputs, each of which can be a logic 0 or 1. With four second keying inputs, the system will be able to distinguish between sixteen different probes.

Probe 246 may be a handheld tool and a user moves the probe from one point to another to make measurements. However, in some applications, probe 246 is part of an endoscopic instrument, robotic instrument, a part of an instrument that inserts inside a body, or any combination of these. For example, the probe is moved or operated using a guiding interface, which may or may not include haptic technology.

In various implementations, the system is powered using a wall outlet or battery powered, or both. Block 251 shows a power block of the system having both AC and battery power options. In an implementation, the system includes an AC-DC converter 253. The converter takes AC power from a wall socket, converts AC power to DC power, and the DC output is connected to the components of the system needing power (indicated by an arrow 254). In an implementation, the system is battery operated. The DC output of a battery 256 is connected to the components of the system needing power (indicated by an arrow 257). The battery is recharged using a recharger circuit 259, which received DC power from an AC-DC converter. The AC-DC converter and recharger circuit may be combined into a single circuit.

The nonvolatile memory may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

The processor may include multiple processors or a multicore processor, which may permit parallel processing of information. Further, the system may also be part of a distributed environment. In a distributed environment, individual systems are connected to a network and are available to lend resources to another system in the network as needed. For example, a single system unit may be used to collect results from numerous sensor probes at different locations.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, Matlab (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows CE, Windows Mobile), Linux, HP-UX, UNIX, Sun OS, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may interface to other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or other device (e.g., laptop computer, smartphone, or personal digital assistant), a user accesses a system of the invention through a network such as the Internet. The user will be able to see the data being gathered by the machine. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 3A:
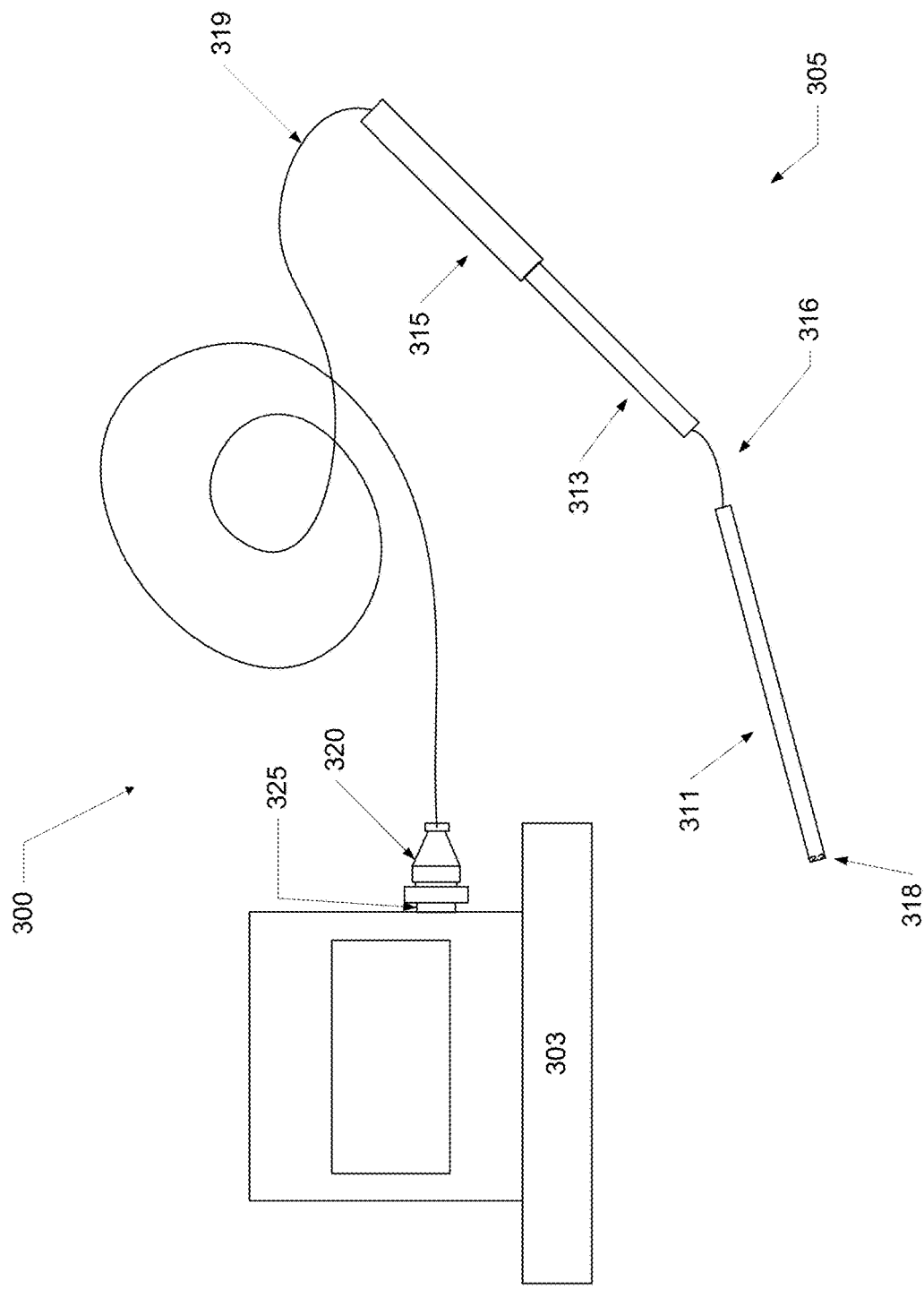
FIG. 3A shows a system of the invention including a monitoring console and a dilator sensor device connected to the console.

FIG. 3A shows one implementation of a system 300 which includes a monitoring console 303 and a dilator sensor device 305. Dilator sensor device 305 includes a series of dilators 311, 313, and 315 (which can be nested) and a sensor probe 316. The sensor probe includes a sensor unit 318 which includes distal ends of conductors (e.g., optical fibers, electrical wires, or both) which is located at a tip of dilator 311. The sensor probe also includes a connector 320 which includes proximal ends of the conductors, and a cable 319 which contains the rest of the conductors in a cable jacket. The connector is removably attached to a receptacle 325 which is affixed to or mounted on the monitoring console.

A dilator refers to a long penetration instrument with an axial lumen which can be used to dilate or enlarge an incision through the skin and subcutaneous layers. It can include a single component or a series of multiple components as shown in FIG. 3A.

The series of dilators 311, 313, and 315 have successively larger diameters. The dilators are sequentially introduced into an incision through the skin and subcutaneously layers to dilate or enlarge the incision. For instance, a surgeon may introduce dilator 311, followed by dilator 313 and then dilator 315. The gradual enlargement of the incision reduces a trauma to the tissue surrounding the incision, and the enlargement of the incision allows surgical tools to be introduced into the body cavity. The dilators are dimensioned such that smaller dilators can be nested inside larger dilators. For example, dilator 311 can be fully inserted inside dilator 313, and dilator 313 can be fully inserted into dilator 315.

In a specific implementation, for example, the smallest dilator 311 may have an outer diameter of 6 millimeter, an inner diameter of 2 millimeters, and the length of 260 millimeters. The intermediate dilator 313 may have an outer diameter of 9 millimeters, an inner diameter of 6.5 millimeters, and the length of 220 millimeters. The largest dilator 315 may have an outer diameter of 12 millimeters, an inner diameter of 9.5 millimeters, and the length of 195 millimeters. These dilator dimensions are merely exemplary, and dilators having different outer and inner diameters and lengths may be used in embodiments of the invention. Furthermore, while each dilator in the series can have a different length, in other implementations, the dilators may have the same length.

While FIG. 3A illustrates an embodiment with three dilators in series, it is to be readily appreciated that embodiments of the invention may include any suitable number of dilators (e.g., 2, 4, 5, 6, 8, 10, and other numbers). If a small surgical corridor is required for a particular surgery, then the smallest dilator alone may be inserted through the patient's skin and subcutaneous layers to provide a surgical corridor. When a larger surgical corridor is desired, then two, three, four, or more successively larger dilators can be introduced sequentially to bluntly dilate an opening provided by the smallest or initial dilator.

Alternatively, a dilator may be a radially expandable dilator where a single dilator tube is radially expandable from a small diameter configuration to a large diameter configuration. In this embodiment, a dilator can be introduced into the body with a small diameter configuration. When the tip of the dilator reaches a target surgical site, the dilator can be radially expanded by inserting an expansion member inside the axial lumen of the dilator. Any suitable radially expandable dilators may be used in embodiments of the invention, including those described in U.S. Pat. No. 5,183,464, which is incorporated by reference in this application.

A dilator can be made of any suitable biocompatible material. The term "biocompatible material" is used in this application in its broadest sense and refers to a material which is used in situations where it comes into contact with the cells and/or bodily fluids of living animals and humans. It is desired that the selected biocompatible material is chemically inert, and thermally and mechanically stable. A dilator can be made of a metal (e.g., stainless steel, aluminum, and others), a polymeric material, or a combination of both. In a specific implementation, a dilator is made of a hollow metal tube which is insulated with a polymeric material.

Sensor unit 318 includes distal ends of conductors such as optical fibers. The distal ends of the conductors are arranged in a particular pattern (which are described more in detail in FIGS. 5A through 6D), and they include at least one source structure and at least one detector structure. A source structure is a structure in the sensor unit that provides and transmits light into a tissue. The source structure can generate light, or it can be a structural component that transmits light generated elsewhere (e.g., from an upstream source). A detector structure is a structure in the sensor unit that detects light (or that is a structural component of the detection process) which is scattered and reflected from the tissue.

In one embodiment, a source structure can be a laser or light emitting diode (LED) that emits a light of a specific wavelength suitable to monitor oxygen saturation. A detector structure can be a photodiode (e.g., a PN diode, a PIN diode, or an avalanche diode) that detects the light transmitted and reflected from a tissue, after the source structure emits the light into the tissue. In a sensor unit, both LEDs and photodiodes are located at the scanning surface of the sensor unit. These LEDs and photodiodes can then be electrically connected to a system unit or console. In this embodiment, since the light is generated next to the tissue surface and subsequently detected at the tissue surface, there is less attenuation of a signal.

In another embodiment, a source structure is an opening in a sensor unit (at its scanning surface) with an optical fiber inside, which is connected to an emitter located elsewhere (e.g., system unit). Likewise, a detector structure is an opening in a sensor unit (at its scanning surface) with an optical fiber inside, which is connected to a detector located elsewhere. The optical fibers from each sensor unit are then connected to either an emitter or a detector which may be located in a system unit or console.

In embodiments of the invention, the cable contains conductors (e.g., optical fibers) in a cable jacket and connects the sensor unit to a connector which couples a sensor probe to a monitoring console. The length of the cable may vary. In a specific implementation, the length of the cable ranges from about 1.2 meters to about 3 meters. For example, the cable may be about 1.3, 1.4, 1.5, 1.6, 1.7, 1.8, 1.9, 2, 2.1, 2.2, 2.3, 2.4, or 2.5 meters long or greater. Depending on the specific application, the cable length may be less than 1.2 meters. In some applications, the cable length will be greater than 3 meters. It may be desirable to use longer cables when a patient is immune compromised and needs to be kept away from sources of contamination, such as a console.

In an implementation, the cable includes one or more optical wave guides enclosed in a flexible cable jacket. The optical wave guides may be used to transmit light from the console, through the sensor unit and into the tissue. The optical wave guides may also be used to transmit the light received from the tissue back to the console.

The optical wave guides may have the shape of a polygon, such as a square, rectangle, triangle, or other shape. In other cases, the optical wave guides may have circular or oval shapes. In a specific implementation, the optical wave guides are multiple strands of fiber optic cable or optical fiber. The flexible cable jacket may be thin-walled PVC with or without an aluminum helical monocoil, shrink wrap tubing, plastic, rubber, or vinyl.

In a specific embodiment, all of the fiber optic cables are enclosed within one end, or both ends of the flexible cable jacket. Minimizing the number of exposed cables lowers the likelihood that the cables will get entangled. In another embodiment, the fiber optic cables are not enclosed together and instead each fiber optic cable is enclosed in its own flexible cable jacket.

In a specific implementation, the cable is passive. For example, it will not contain any active, generative properties to maintain signal integrity. However, in other implementations, the cable may include active components. The cable may include active components to amplify the signal transmitted through the sensor unit, received at the sensor unit, or both. For example, long lengths of cable subject to significant attenuation may require amplification. Amplification may also be required if the monitored site contains a particularly dense structure such as bone. In a specific implementation, radiation sources such as light emitting diodes (LEDs) may be placed in the sensor unit. Thus, the cable may contain electrical wiring to transmit power to the radiation sources.

In an embodiment of the invention, each opening on the sensor unit and corresponding cable is dedicated to a particular purpose. For example, a first opening on the sensor unit (and corresponding fiber optic cable) is dedicated to transmitting light from the monitoring console. A second opening on the sensor unit is dedicated to transmitting a signal received at the second opening to the monitoring console.

Some embodiments use a particular opening and cable for multiple purposes (e.g., both input and output) using a scheme such as multiplexing.

In a specific embodiment, a particular opening and cable transmits an output to affect a reaction (e.g., sending electrical signals to stimulate muscle, nerve, or other tissue). Another opening and cable transmits the resultant signal back to the monitoring device. In yet another embodiment, the openings and cables may simply detect changes and transmit these changes back to the monitoring device. For example, the openings and cables may carry voltage changes in the patient's tissue back to the monitoring device.

Connector 320 at the end of the cable attaches the sensor probe to its receptacle on the console. The connector also protects the cable from accidental disconnection. The connector may include a collar that threads onto the receptacle on the console. Alternatively, the connector may include a lug closure, press-fit, or snap-fit components.

In a specific implementation, the console can provide alerts to the user when a proper connection is made between the sensor probe and the console. The alerts may be visual (e.g., a flashing light on a display of console), audible, or both. The display monitor may also show a type of sensor device (e.g., dilator sensor device, needle sensor device, and others) that is attached to the console, as well as other information.

In a specific implementation, there may be other connectors on the cable besides connector 320 and receptacle 325. These other connectors allow the cable to be separated into two or more pieces, allowing additional lengths of cable to be attached, or both. Additional connectors allow the overall length of the cable to be adjusted as necessary. Furthermore, only a portion of the cable that is contaminated can be disconnected and disposed, rather than disposing the entire length of the cable after each use.

In one implementation, console 303 (sometimes referred to as a monitoring console or system unit) shown in FIG. 3A can be a portable console which may be hand carried. A portable console can follow a patient and optical measurements can be made anywhere in the hospital. In this implementation, it is desirable that the portable console is battery operated. In another implementation, the console may be a large, nonportable device that is attached to a wall or secured to a stand. In this implementation, the system is typically connected to AC power.

The console may include a mass storage device to store data. Mass storage devices may include mass disk drives, floppy disks, magnetic disks, optical media, phase-change media, fixed disks, hard disks, CD-ROM and CD-RW drives, DVD-ROM and DVD-RW drives, flash and other nonvolatile solid-state storage drives, tape storage, reader, and other similar devices, and combinations of these.

The stored data may include patient information. This includes, for example, the patient's name, social security number, or other identifying information, measurements of light returned from the patient's tissue, oxygen saturation, total hemoglobin concentration, blood flow, pulse, signal quality, and the time and date of measurements. The measurements of various physiological parameters may include high, low, and average values and elapsed time between measurements.

The above drives may also be used to update software in the console. The console may receive software updates via a communication network such as the Internet.

In an implementation, the console also includes an interface for transferring data to another device such as a computer. The interface may be a serial, parallel, universal serial bus (USB) port, RS-232 port, printer port, and the like. The interface may also be adapted for wireless transfer and download, such as an infrared port. The system transfers data without interruption in the monitoring of the patient.

The console also includes a display screen which may display the patient's data, such as measurements of light returned from the patient's tissue, oxygen saturation, total hemoglobin concentration, blood flow, pulse, signal quality, or any combinations of these parameters. The screen may be a flat panel display or include a touch screen interface so that the user can input data into the console.

The console, in addition to the display, may also include a processor, signal emitter circuit, signal detector circuit, and a receptacle to removably couple ends of one or more conductors. In a specific implementation, the ends of one or more conductors (e.g., optical fibers or electrical wires) are instead permanently connected to the console. The signal emitter circuit may operate to send a signal through the one or more conductors. The signal detector circuit then receives a signal via one or more conductors.

In a specific implementation, the signal emitter circuit may include one or more laser emitters, light emitting diode (LED) emitters, or both. The signal emitter circuit may be used to generate an optical signal having two or more different wavelengths to be transmitted through the sensor unit. The wavelengths may range from about 600 nanometers to about 900 nanometers.

In a specific implementation, the console includes a first radiation source and a second radiation source. The radiation sources may be dual wavelength light sources. In other words, first radiation source provides two wavelengths of radiation and second radiation source provides two wavelengths of radiation. First radiation source, second radiation source, or both may include one or more laser diodes or light emitting diodes (LEDs) that produce light in any wavelength, but typically the wavelengths range from about 600 nanometers to about 900 nanometers. In a specific implementation, a first wavelength of light is generated that has a wavelength of about 690 nanometers. A second wavelength of light is generated that has a wavelength of about 830 nanometers.

In a specific implementation, one or more near-infrared radiation sources are included within the console. In other implementations, the radiation sources may be external to the console. For example, the radiation sources may be contained within a separate unit between the console and sensor probe. The radiation sources may, for example, be contained in a sensor probe or sensor unit itself or in other parts (e.g., in the console). In yet another implementation, some radiation sources may be within the console while other radiation sources are external to the console.

These radiation sources may be near-infrared lasers. In a specific implementation, there is one near-infrared laser located within the console. In other implementations, there may be more than one near-infrared laser. For example, there may be 2, 3, 4, 5, 6, 7, 8, 9, or 10, or more than 10 radiation sources. In another implementation, the radiation sources may include those that produce a visible light.

Also, only a percentage of the power output of the source is transmitted to the tissue. For example, when the laser diode output is 30 milliwatts, the power that gets to the tissue will be about 3 milliwatts. So, approximately 1/10 of the power of the laser diode is transmitted into the tissue.

In a specific implementation, a single pulse of light is transmitted into the tissue. In another implementation, multiple pulses of light may be transmitted into the tissue. For example, a first pulse of light may be received by a first detector. A second pulse of light may be received by a second detector.

In a specific implementation, light emitted by different radiation sources is provided to a beam combiner via optical fibers. The beam combiner effectively merges the light from different radiation sources, and the merged light is then provided via output optical fibers. The output fibers are arranged to allow the merged or combined light to be homogenized to ensure that the light is substantially uniformly distributed across the output fibers when the light enters the sensor unit. The beam combiner may be located in the console, or may be located outside of the console.

Figure 3B:
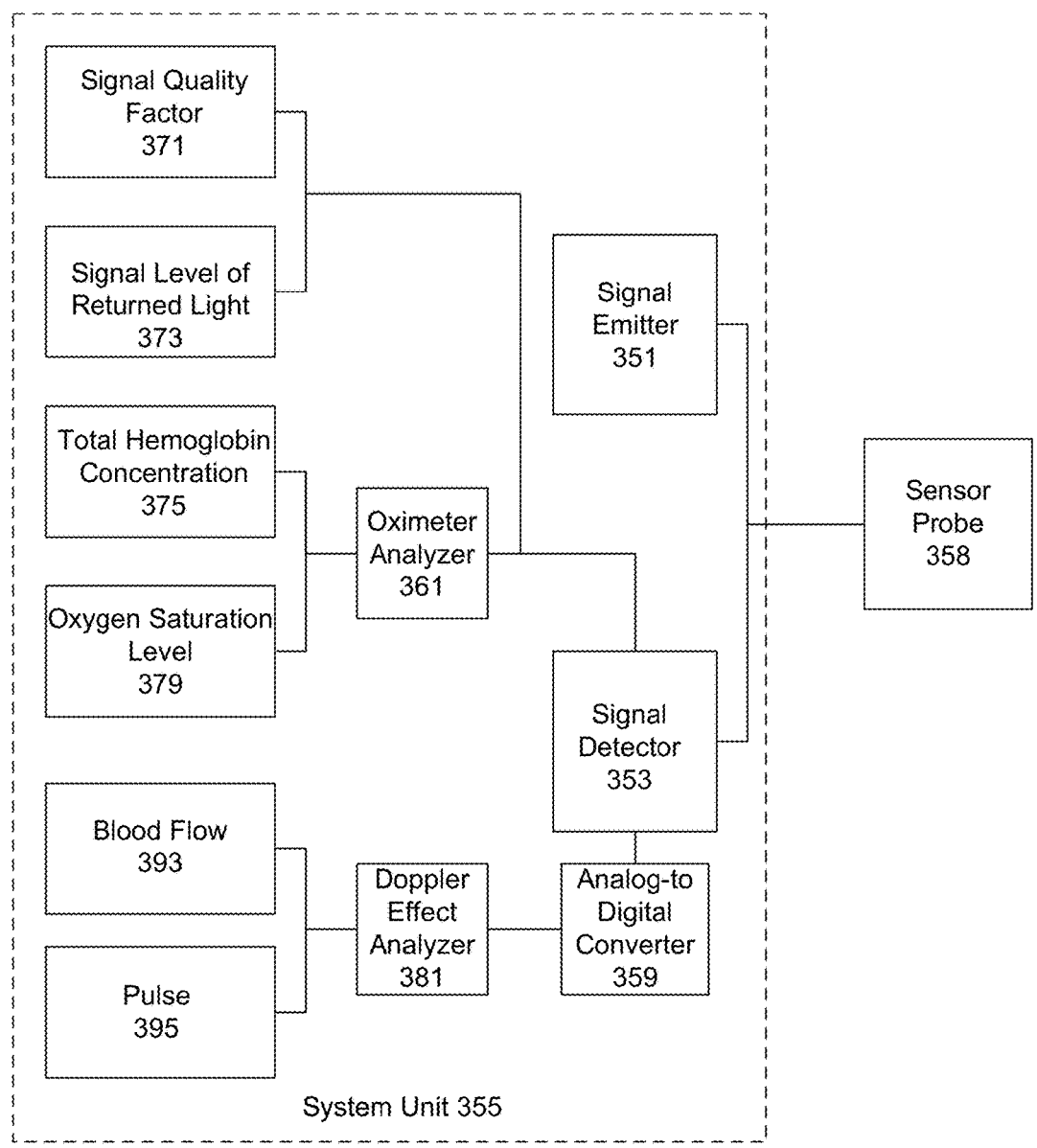
FIG. 3B shows a block diagram of a system where various parameters of tissue contacted by a sensor probe can be measured and calculated to determine the presence or absence of a blood vessel at the tip of the sensor probe.

FIG. 3B shows a specific implementation of a monitoring system in accordance with the present invention. As shown, a sensor probe 358 (e.g., a sensor probe which is a part of a dilator sensor device) is connected to a system unit 355. The system unit includes a signal emitter 351, a signal detector 353, an analog-to-digital converter 359, an oximeter analyzer 361, a Doppler effect analyzer 381, and a number of output parameters. These output parameters include a signal quality factor 371, a signal level of returned light 373, a total hemoglobin concentration 375, an oxygen saturation level 379, a blood flow 393, and a pulse 395.

These components may be housed within a single housing. Alternatively, these components may be housed in separate housings. Different implementations of the system may include any number of the components described, in any combination or configuration, and may also include other components not shown.

Signal emitter 351 emits light of a suitable wavelength or wavelengths into sensor probe 358 through source fibers into a tissue where optical measurements are desired. When light is transmitted to a target tissue via source structures in the sensor unit, light scatters due to heterogeneous structure of the tissue, and some of the light is absorbed by chromophores such as hemoglobin. An attenuated version of the light that is reflected by the tissue is detected by detector structures in the sensor unit and is transmitted to signal detector 353 in the system unit. Also, due to Doppler effect, the frequency of the reflected light is broadened and the frequency of the reflected light will be broader than the frequency spectrum of the original light. These changes are also detected by signal detector 353.

From optical measurements obtained from the signal detector, a signal quality factor 371 (sometimes referred to as a Q factor in other applications) can be obtained. The signal quality factor is a parameter that is associated with the ratios of optical measurements from the sensor head. The calculated signal quality factor can vary from 0 to 1 (sometimes scaled and displayed from to 0 to 100). When the signal quality factor is approximately 1 (or 100 when scaled up), this indicates that the sensor unit is in good contact with tissue, that the tissue is highly homogeneous, and that the sensor probe is in good working order. While the signal quality factor is not used as an indicator for presence or absence of blood vessels proximal to the tip of the device, the signal quality factor indicates the quality of signal obtained from the signal detector. Discussions of a Q factor or a signal quality factor can be found in U.S. patent application Ser. No. 11/162,380, filed Sep. 8, 2005, which is incorporated by reference.

The changes in the intensity and frequency spectrum of returned light is analyzed by oximeter analyzer 361 and Doppler effect analyzer 381. From these analyses, a number of different parameters can be calculated. One or combinations of parameters will help a surgeon to determine whether there is a blood vessel nearby or at the tip of the sensor probe (e.g., at the tip of the dilator sensor device).

Oximeter analysis 361 calculates oxygen saturation level or value ($StO_2$) 379, hemoglobin concentration (deoxyhemoglobin, oxyhemoglobin, or total hemoglobin) 375, or both. The calculations are based on a value of the initial light generated by the signal emitter and a value of an attenuated version of the light that is reflected from the tissue and is subsequently detected by the signal detector. The term oxygen saturation level (or value) refers to the percentage of hemoglobin that is bound to oxygen at the time of measurement. Additional details on attenuation methods are also discussed in U.S. patent application Ser. No. 12/126,860, filed May 24, 2008, which is incorporated by reference. The attenuation ratio method may also include techniques discussed in U.S. Pat. No. 6,587,701, which is incorporated by reference.

In the automatic error-cancellation or self-calibration scheme, the system factors such as source intensity, detector gain, and loss of light in the optical fibers and connectors are cancelled automatically. The automatic error-cancellation scheme is discussed in more detail as equations 5a and 5b in U.S. Pat. No. 6,597,931, which is incorporated by reference. The self-calibration scheme may also include equations discussed in U.S. Pat. Nos. 6,516,209, 6,735,458, and 6,078,833, U.S. patent application Ser. No. 12/126,860, filed May 24, 2008, and *New Optical Probe Designs for Absolute (Self-Calibrating) NIR Tissue Hemoglobin Measurements*, Proc. SPIE 3597, pages 618-31 (1999), which are incorporated by reference.

A blood vessel can be distinguished from nonvascular surrounding tissue according to the sensor measurements, because it is expected that the blood vessel contains a higher number of blood cells (and thus a higher concentration of hemoglobin) and thus richly oxygenated compare to nonvascular surrounding tissues. Thus, if there is a blood vessel nearby or at the tip of a sensor unit, then it is expected that the oxygen saturation level, total hemoglobin concentration, or both measured by the system will be higher than nonvascular surrounding tissue.

Signal level of returned light 373 can also be used as an indicator of whether a blood vessel is nearby or at the tip of the dilator sensor device. A large blood vessel filled with blood will absorb infrared and visible red light more than the nonvascular surrounding tissue. Thus, it is expected that the signal level of returned light if the sensor unit is contacting a blood vessel is significantly lower (e.g., at least 20 percent lower) than the surrounding nonvascular tissue.

Doppler effect analyzer 381 can calculate blood flow 393 and pulse 395. These two parameters can also be used as indicators whether there is a blood vessel at the tip of a dilator sensor device. Both arteries and veins have significantly higher blood flow than surrounding soft tissue and nonvascular structures such as tendon and fascia. Also, a major artery is distinguishable from other structures because it has a pulse. Thus, the blood flow and pulse can also be used as additional parameters to determine the presence of a blood vessel at the tip of the dilator sensor device.

The Doppler effect analyzer analyses the intensity and spectrum change of light when it is transmitted and reflected from a tissue. Laser light is scattered by the red blood cells in the capillaries and the tissue surrounding the capillaries.

The velocity of the blood flow, which runs in all directions in the capillary network, has velocity distribution averaging at 1 millimeter per second or less. The tissue scattering cross section is much greater than that of the moving red blood cells. Based on this information, the following calculations can be obtained.

The fluctuating intensity of the light that is scattered to the detector, i.e. the signal, can be written as $$P(\omega) = i_0^2 \delta(\omega) + \frac{Ci_0}{\pi} + i_0^2 S(\omega), \quad (1)$$

where $i_o$ is the mean detected intensity, $S(\omega)$ is the spectrum, and C is a constant.

The first moment of $S(\omega)$ is the mean Doppler shift, $$\langle \omega \rangle = \int_{-\infty}^{\infty} |\omega| S(\omega) d\omega \bigg/ \int_{-\infty}^{\infty} S(\omega) d\omega. \quad (2)$$

The mean Doppler shift is proportional to the rms speed of the moving particles $\sqrt{\langle V^2 \rangle}$ as $$\langle \omega \rangle = F(\langle V^2 \rangle^{1/2}, a, \overline{m}) = \langle V^2 \rangle^{1/2} \times \frac{1}{a} \times \left[ \frac{1}{(12\xi)^{1/2}} \beta f(\overline{m}) \right] \quad (3)$$

where V is the velocity of the moving RBC, a represents the size of the scatter (i.e. the radius of spherical scatter or radius of RBC disc), ξ is an empirical factor which is related to the shape of the cells, β=0.17 is a constant, $\overline{m}$ is the mean number of scattering of photon with RBC, and $f(\overline{m})$ is a function of $\overline{m}$ only. $f(\overline{m})$ can be expressed as follows $$f(\overline{m}) = \frac{2}{\pi^{1/2}} \exp(-2\overline{m}) \sum_{j=1}^{\infty} \frac{(2\overline{m})^j \Gamma(j+1/2)}{\Gamma(j+1)\Gamma(j)} \propto \begin{cases} \overline{m} \text{ if } \overline{m} \leq 1 \\ (\overline{m})^{1/2} \text{ if } \overline{m} \geq 2m \end{cases}. \quad (4)$$

It is noted that the typical values of the quantities in Eq. (3) are as follows: V~0.2-2.0 mm/sec, a<0.15 μm~1.2, ξ0.1 and β=0.17.

The mean number $\overline{m}$ of scattering of photon with RBC in (3) should be proportional to the total hemoglobin concentration. Replacing $\overline{m}$ by Hgb, we have $$\langle V^2 \rangle^{1/2} \propto \langle \omega \rangle \times \begin{cases} Hgb \text{ if } Hgb \text{ small} \\ Hgb^{1/2} \text{ if } Hgb \text{ large} \end{cases}. \quad (5)$$

By using the above equations as a guide for calibration, the blood flow can be calculated. The pulse can also be derived from Doppler blood flow measurements. Some general discussions of Doppler flowmetry and estimating blood flow can be found in P. Elter et al., "Noninvasive, real time laser Doppler flowmetry in perfusion regions and larger vessels", SPIE Proceeding Vol. 3570, pages 244-54, Stockholm, Sweden, 1998; R. Bonner et al., "Model for laser Doppler measurements of blood flow in tissue", Applied Optics, Vol. 20, No. 12, 1981. These publications are incorporated by reference in this application.

The blood flow may also be calculated using laser Doppler flowmetry (LDF). The flow curve obtained may be noisy, and a smooth filtering may be applied to the flow curve before calculating a pulse rate from the flow curve. The Savitzky-Golay (S-G) smoothing filter in time domain may be applied to the data obtained in the flow curve. The S-G filter is described in Savitzky and Golay, *Analytical Chemistry*, Vol. 36, pp. 1627-39 (1964), which is incorporated by reference in this application.

The S-G filter is applied to a series of equally spaced data values $f_i = f(t_i)$, where $t_i \equiv t_0 + i\Delta$, for some constant sample time spacing Δ and i= . . . −2, −1, 0, 1, 2, . . . . The S-G filter replaces each $f_i$ by a linear combination $g_i$ of itself and some number of nearby neighbors, $$g_i = \sum_{n=-n_L}^{n_R} c_n f_{i+n} \quad (6)$$

In equation (6), $n_L$ is the number of points used "to the left" of a data point i (i.e., earlier than it), while $n_R$ is the number used to the right (i.e., later). The S-G filter approximates the underlying function within the moving window by a polynomial, typically quadratic (the $1^{st}$ order) or quartic (the $2^{nd}$ order). For each point $f_i$, it least-squares fits a polynomial to all $n_L+n_R+1$ points in the moving window, and then set $g_i$ to be the value of that polynomial at point i. The 0-th order S-G filter is also called moving window averaging, which, by letting $g_i$ in equation (6) be a linear combination of $f_i$s with equal weight, i.e., setting $c_n=1/(n_L+n_R+1)$.

The pulse rate can be calculated from the flow curve in time domain by using the following steps. The S-G filter is used to smooth the blood flow curve (i.e., a graph of sample time points on X-axis and blood flow in arbitrary units on the Y-axis), resulting in a secondary smoothed flow curve. In an implementation, this S-G filter may be of 0-th order and with $n_R=0$. In some other embodiments, a higher-order S-G filter may be used.

Then the time difference between any two adjacent peaks of the smoothed flow curve is determined. This time difference is the pulse duration. The pulse duration may then be converted into a pulse rate. Finally, the average pulse rate can be calculated among given number of pulse rates. The average pulse rate can then be used to determine if there is a blood vessel at the tip of the sensor probe.

A suitable sampling rate can be selected to measure various parameters of the tissue. For monitoring multiple parameters (including oxygen saturation level, hemoglobin concentration, signal level of returned light, blood flow and pulse rate), the system or console may include an analog-to-digital converter 359 for fast data sampling desired for blood flow measurement. For measuring blood flow and pulse, at least one of the radiation sources is continuously on while one of the detectors collects signals at a fast sampling rate. For example, a sampling rate of about two kilohertz (i.e., one sampling per half second) may be used to determine oxygen saturation level or hemoglobin concentration of tissue. On the other hand, a sampling of about 100 kilohertz (i.e., one sampling per 0.01 millisecond) may be used to determine the blood flow and pulse rate of tissue.

As an illustration, to obtain an oxygen saturation level and a total hemoglobin concentration, a software in the console may send an "X" command to collect oximeter raw data (e.g., intensity of returned light at all the detectors after each of the source emitted) by sampling, for example, once each 10 seconds. In addition, the software may send multiple "C" commands. The "C" commands may send additional 150 emissions via laser diode S1 (at 830 nanometers once every 0.07 seconds) between two successive X commands to measure the blood flow and pulse. The signals from additional laser Doppler flowmetry emissions received by one of the photodiodes (e.g., detector structure D2) may be, with a much higher rate (e.g., 25 kilohertz), transferred to digital information and may be recorded in a separate data file for further analysis. These sampling rates are exemplary, and other suitable sampling rates may be used to collect data.

Any one or combinations of parameters described above can be combined to formulate an overall indicator or index for blood vessel existence in front of the tip of the sensor probe or dilator sensor device. In one implementation, the signal level of returned light and blood flow parameters may be combined to formulate an indicator for blood vessel existence. In another implementation, the signal level of returned light, total hemoglobin concentration, and blood flow parameters may be combined to formulate an indicator for blood vessel existence. In yet another implementation, total hemoglobin concentration, blood flow, and pulse parameters may be combined to formulate an indicator for blood vessel existence. In yet another implementation, all five parameters (i.e., the signal level of returned light, total hemoglobin concentration, oxygen saturation level, blood flow, and pulse) may be combined to formulate an indicator for blood vessel existence.

The measured parameters for regions containing arteries and veins or nonvascular tissue will be different. For the signal level of returned light, a large vessel filled with blood exhibits a stronger absorption of near infrared and visible red light than the surrounding nonvascular tissue. A region containing a large blood vessel also contains a higher concentration of hemoglobin than the surrounding tissue. A region containing a large artery exhibits a higher tissue oxygen saturation than the surrounding tissue, and a region containing a large vein exhibits a lower oxygen saturation than the surrounding tissue under normal physiologic conditions. Both arteries and veins exhibit significantly higher blood flow than surrounding soft tissue and nonvascular structures such as tendon and fascia. A major artery should be distinguishable from other structures by the presence of pulse.

Accordingly, the arteries will exhibit relatively high oxygen saturation level, a high level of hemoglobin concentration, a high level of near infrared absorption (and thus a lower signal level of returned light), a strong pulse, and a substantially high blood flow.

Like the arteries, the veins will exhibit a high level of hemoglobin concentration, a high level of near infrared absorption (and thus a lower signal level of returned light), and a substantially high blood flow. However, the veins will exhibit a relatively lower oxygen saturation level and a minimal pulse.

Nonvascular surrounding tissues will exhibit a relatively lower hemoglobin concentration, a relatively lower near infrared and visible red light absorption (and thus a higher signal level of returned light), no pulse, and a substantially low blood flow.

Based on the differences described above, the software in the console can formulate an overall indicator or index for blood vessel existence (or for vessel avoidance) in front of the tip of the sensor probe.

By a way of example, if the calculated oxygen saturation level is greater than X percent, if the measured blood flow is greater than Y units, and if the total hemoglobin concentration is greater than Z grams per deciliter (g/dL), then the console may determine that it is a positive indicator for blood vessel existence at the tip of a sensor probe. In another example, if the measured blood flow is greater than U units, if the pulse is greater than V units, and if the signal level of returned light is lower than W units, then it may be a positive indicator for blood vessel existence at the tip of a sensor probe.

For instance, it may be a positive indicator for blood vessel existence at the tip of a sensor probe: (1) if the blood flow trend curve is pulsatile; (2) if the calculated pulse rate is stable in the range between about 50 to 120 pulses per minute; (3) the relative change in hemoglobin concentration or the relative change in signal level is greater than a preset value (e.g., 20 percent) in comparison to measurements obtained when the tip of the sensor probe was in a previous location (e.g., 2 millimeters away from the current location); or (4) any combination of above.

In a specific implementation, the console may provide alerts when there is a positive indicator for a blood vessel existence based on one or more parameters measured by the monitoring system. As a doctor advances a dilator sensor device towards a target surgical location inside the body, a doctor can quickly respond to the alerts by stop advancing the dilator sensor device towards a blood vessel. A doctor can manipulate and maneuver the dilator sensor device away from the blood vessel and redirect the dilator sensor device towards the target surgical location via another route.

The alerts may be visual (e.g., a flashing light on a display of the console), audible, or both. Visual alerts may be designed so that they are viewable from any location (e.g., a flashing light on the top of the console). Visual alerts can be a flashing light or flashing display of individual parameters or a positive indicator of a blood vessel on a display. Audible alerts allow the doctor to focus on the surgical site without having to look away from the patient. Audible alerts can vary in intensity and sounds, depending on an overall indicator value for the existence of a blood vessel. Different sets of alerts can be used depending on the level of indicator for the blood vessel existence determined by the system. Different alerts include different colors, sounds, and intensities of colors and sounds.

The alerts may be user programmable. That is, users may set which alerts are enabled, the threshold at which they are activated, and the intensities of the alerts. For example, a doctor may decide to enable the oxygen saturation alert, set the alert to occur if and when the blood flow level rises above a certain value, and set the volume level of the alert.

FIG. 4A illustrates another implementation of a dilator sensor device 401. FIG. 4B illustrates a longitudinal cross section of a tip of the dilator sensor device shown in FIG. 4A. Dilator sensor device 401 includes a dilator 405 and a sensor probe 416. The sensor probe includes a sensor unit 418 at the tip of the dilator which includes distal ends of optical fibers 431 and a connector 420 which includes proximal ends of the optical fibers, and a cable 409 which encases the optical fibers in a cable jacket. In FIG. 4A, the connector is disassociated to show proximal end portions of optical fibers 431. In the embodiment shown in FIG. 4A, the optical fibers run continuously from the sensor unit to the connector.

In a specific implementation, dilator 405 is made of a hollow metal tube which is coated with a polymeric material on its outer surface except two regions. Typically, a triangular marking 406 in a tip 411 of the dilator and a neck region 408 are not covered with a polymeric material, and metal portions of the hollow metal tube are exposed. Neck region 408 of the dilator can be electrically coupled with a nerve monitoring system (not shown), and triangular marking 406 in tip 411 of the dilator can be used to transmit current into a tissue contacting the tip of the dilator to detect the location of a nerve present nearby the tissue. The rest of the dilator is coated with a polymeric material to prevent shunting. A nerve monitoring system is described more in detail along with FIGS. 9 and 10.

In a specific implementation, dilator 405 includes a triangular marking 406 pointing towards the tip of the dilator and depth markings 407. The triangular marking is useful to indicate the orientation of light source-detector geometry on the sensor surface at the tip. Neck region 408 may also include a marking line parallel to the axis (not shown in FIG. 4A which is aligned with the arrow of triangular marking 406). When tip 411 is inserted into human body, this marking line on neck region 408 assists a surgeon in determining the orientation of the arrow of triangular marking 406 (for nerve avoidance) and the orientation of the light source-detector geometry on the sensor surface (for blood vessel avoidance). The triangular marking may also assist in aligning larger sequential dilators with the initial dilator.

The depth markings in dilator 405 may be separated by a regular interval, typically about 10 millimeters apart. The depth markings written at each interval represent a distance from the tip of the dilator to the location of the depth marking. The depth markings are helpful for a surgeon to determine how deeply a dilator has penetrated inside the body and the location of a target surgical location. Based on the depth of a target surgical location, the surgeon can utilize surgical tools of appropriate lengths to perform surgical procedures.

As shown in FIG. 4B, the tip of the dilator sensor device has sensor unit 418 (sometimes referred to as a sensor head) which includes a cylindrical block 421 with four channels extending along the longitudinal axis of the cylindrical block and distal end portions of optical fibers 431a, 431b, 431c, and 431d inserted into each channel in the cylindrical block. The channels in the cylindrical block separate and fix distal ends of the optical fibers by a suitable distance to optimize optical measurements for a given tissue. The cylindrical block may extend the entire length of the dilator; alternatively, the cylindrical block may be present only at the distal end of the dilator, as shown in FIG. 4B, to firmly fix the distal end portions of the optical fibers.

Any suitable cylindrical block material can be used as long as it is chemically and structurally stable, and does not interfere with transmission of optical signals in the optical fibers. For example, the cylindrical block can be made of an aluminum alloy (e.g., 6061 aluminum alloy) with channels for threading optical fibers through. Then the aluminum alloy cylinder can be attached in the inner surface of the dilator at the tip using an adhesive, such as Epotek 353ND epoxy.

In a specific implementation, for a dilator sensor device having an outer diameter of 9 millimeters and an inner diameter (i.e., $d_2$) of 6.5 millimeters, cylindrical block 421 may have a diameter, $d_1$, of 6.45 millimeters, and the length, $l_i$, of 5 millimeters. In this implementation, the cylindrical block is adhesively attached to an inner surface of the dilator. The optical fibers are filled into the holes in the cylindrical block.

FIG. 4C shows another implementation of a dilator sensor device where a sensor probe 446 is slidably coupled to a dilator 445. The sensor probe includes optical fibers 441 which are surrounded by a sheath material 443. The sheath material may be a soft polymeric material. The sensor probe is nonadhesively disposed inside the dilator, and its positioning inside the dilator can be manipulated from its proximal end of the sensor probe.

In some situations, it may be desirable to have a sensor probe which can be independently manipulated and advanced forward or backward inside the dilator. Since a sensor probe has a smaller diameter and may be softer than the tip of dilator, advancing the sensor probe in front of the tip of the dilator may minimize any potential damage to the tissue in the pathway of the dilator sensor device. Furthermore, the sensor probe can be completely removed from the dilator in this implementation, and a surgical tool, such as a K-wire, may be inserted into the dilator.

Figure 5A:
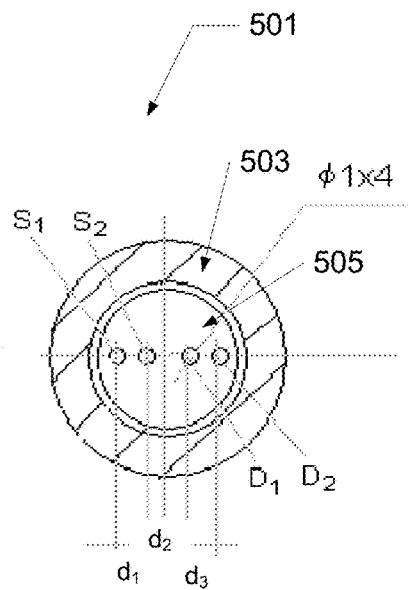
FIG. 5A shows a sensor opening pattern where all four sensor openings are linearly aligned.

FIG. 5A shows a cross section of a tip of a dilator sensor device 501 in accordance with one embodiment of the invention. The cross section of dilator sensor device 501 includes a dilator 503 and a sensor unit 505. The sensor unit includes distal end portions of four optical fibers—two source structures S1 and S2, and two detector structures D1 and D2. The source structures refer to openings in the sensor unit which include source fibers (e.g., optical fibers which transmit light from a light source). The detector structures refer to openings in the sensor unit which include detector fibers (e.g., optical fibers which detect or collect light reflected from a tissue and transmit to a photodetector). The source and detector structures in the sensor unit are sometimes referred to as openings or sensor openings in this application.

The source structures and detector structures may be arranged in any suitable pattern (e.g., the distances between the structures, and their sizes), depending on the type of tissue being examined or the depth of optical measurements desired. Typically, the larger the distance between a source structure and a detector structure, the longer the distance light travels from the source structure until it is detected by the detector structure. Thus, a sensor unit with a larger distance between a source structure and a detector structure can generally measure optical parameters deeper into the tissue.

As shown in FIG. 5A, two source structures S1 and S2 and two detector structures D1 and D2 are all aligned linearly. In a specific implementation, the distances between adjacent sensor structures are all equal. In other words, $d_1$ (a distance between S1 and S2) is equal to $d_2$ (a distance between S2 and D1), and $d_1$ and $d_2$ are equal to $d_3$ (a distance between D1 and D2). In a specific implementation, $d_1$, $d_2$, and $d_3$ are equal to 1.5 millimeters.

Figure 5B:
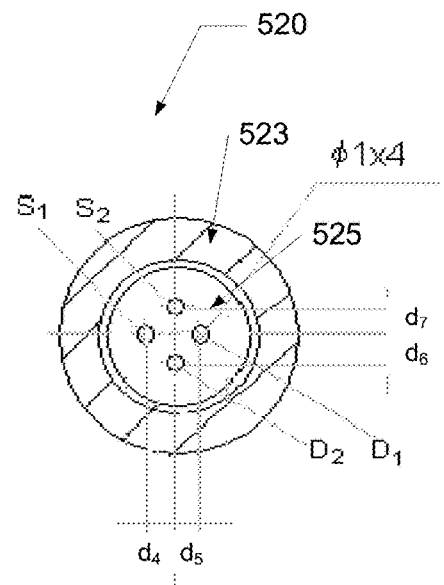
FIG. 5B shows another sensor opening pattern where four sensor openings are spaced from one another and form a diamond array.

FIG. 5B shows a cross section of a tip of another dilator sensor device 520. The cross section of dilator sensor device 520 includes a dilator 523 and a sensor unit 525. The sensor unit includes two source structures S1 and S2 and two detector structures D1 and D2 which are arranged in a symmetrical diamond array. In a specific implementation, $d_4$ (a distance between S1 and the center of the four sensor openings) is 1.5 millimeters; $d_5$ (a distance between D1 and the center of the four sensor openings) is 1.5 millimeters; $d_6$ (a distance between D2 and the center of the four sensor openings) is 1.5 millimeters; and $d_7$ (a distance between S2 and the center of the four sensor openings) is 1.5 millimeters.

Figure 5C:
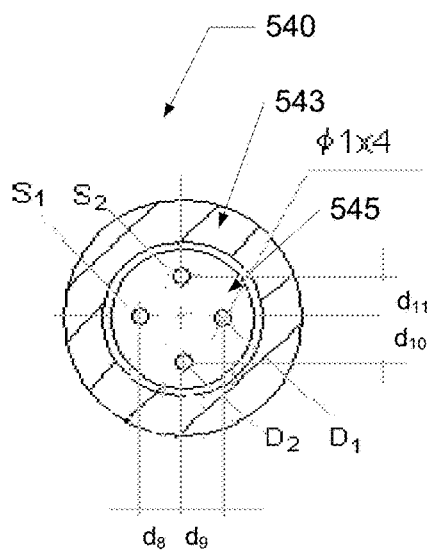
FIG. 5C shows another sensor opening pattern where four sensor openings are spaced from one another and form a larger diamond array than the array shown in FIG. 5B.

FIG. 5C illustrates a cross section of a tip of another dilator sensor device 540. The cross section of dilator sensor device 540 includes a dilator 543 and a sensor unit 545. The sensor unit includes two source structures S1 and S2 and two detector structures D1 and D2 which are arranged in a symmetrical diamond array which is larger in size than the array shown in FIG. 5B. In a specific implementation, $d_8$ (a distance between S1 and the center of the four sensor openings) is 2 millimeters; $d_9$ (a distance between D1 and the center of the four sensor openings) is 2 millimeters; $d_{10}$ (a distance between D2 and the center of the four sensor openings) is 2 millimeters; and $d_{11}$ (a distance between S2 and the center of the four sensor openings) is 2 millimeters.

The distances between sensor opening structures above are exemplary, and embodiments of the invention are not limited to such distances. The separation distance between source structures and detector structures depend on many factors. Generally, a source structure and a detector structure are separated by a larger distance when optical measurements from a deeper volume of tissue are desired.

For example, the human iliac artery has a diameter of about 1 centimeter with a wall thickness of about 1 to 2 millimeters. If a sensor unit as shown in FIG. 5A is used, it may be desirable to use a sensor array with a relatively large source-detector separation (e.g., in the range of between about 1.5 millimeters to 5 millimeters) to provide greater depth of optical measurements.

In embodiments of the invention, optical fibers in the sensor probe typically have a diameter ranging between about 0.5 millimeters to 1.5 millimeters.

In a specific implementation, each of source structures S1 and S2, and detector structures D1 and D2 shown in FIGS. 5A through 5C is an optical fiber bundle with a diameter of 1.0 millimeter which is comprised of borosilicate glass fibers having a diameter of 33 micrometers.

In another implementation, each of source structures and detector structures may include an optical fiber bundle with a diameter of 0.5 millimeters. Using an optical fiber bundle with a smaller diameter is desirable or necessary, particularly when a bore or longitudinal lumen inside a penetration device is small.

In a specific implementation, source structure S1 of a dilator sensor device is aligned with the arrow of a triangular mark (e.g., mark 406 shown in FIG. 4A) at the tip of a dilator sensor device. The triangular mark allows the surgeon to know the source-detector geometry at the tip of the dilator sensor device when the device inserted inside the body. For example, when using a linear array dilator sensor device shown in FIG. 5A, it may be desirable to have the line of S1-S2-D1-D2 to be aligned with a blood vessel to be detected (or to be avoided).

Figure 6A:
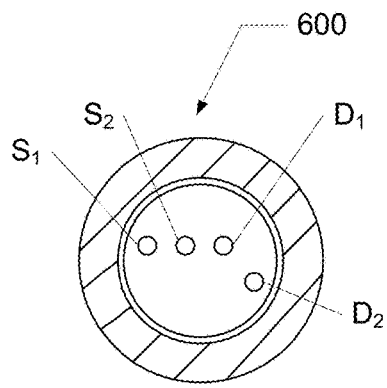
FIG. 6A shows another sensor opening pattern where three sensor openings are linearly aligned and the fourth sensor opening is offset from the other three sensor openings.

FIGS. 6A through 6D illustrate embodiments of the invention with different arrangements of source structures and detector structures at the tip of dilator sensor devices. FIG. 6A illustrates a cross section of a tip of a dilator sensor device 600 with an asymmetric arrangement of source structures and detector structures. In FIG. 6A, source structures S1, S2 and detector structure D1 are aligned linearly, and detector structure D2 is offset from the rest of the sensor openings and are not linearly aligned with openings S1, S2, and D1.

Figure 6B:
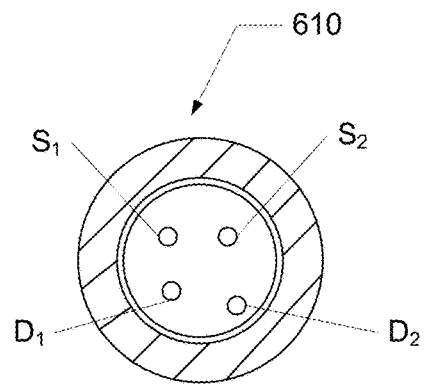
FIG. 6B shows another asymmetric sensor opening pattern where a line drawn through source structures is not parallel to a line drawn through detector structures.

FIG. 6B illustrates another asymmetrical arrangement of sensor openings in a dilator sensor device 610. In FIG. 6B, source structures S1 and S2 and detector structure D1 are all equidistant from the center of the dilator sensor device. Detector structure D2 is farther away from the center of the dilator sensor device compared to other three structures. Also, a line drawn through source structures S1 and S2 is not parallel to a line drawn through detector structures D1 and D2.

Figure 6C:
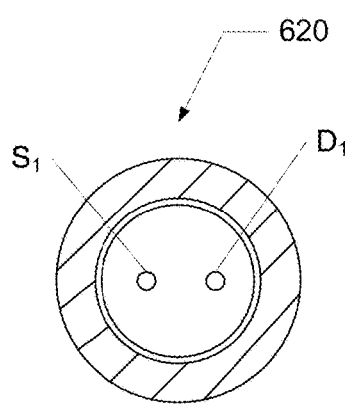
FIG. 6C shows another sensor opening pattern with two sensor openings.

FIG. 6C illustrates a cross section of a tip of a dilator sensor device 620 which has one source structure S1 and one detector structure D1. In an implementation, the distance between S1 and the center of the dilator sensor device is equal to the distance between D1 and the center of the dilator sensor device.

Figure 6D:
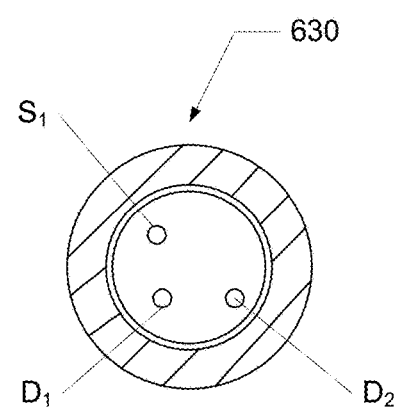
FIG. 6D shows another sensor opening pattern with one source structure and two detector structures.

FIG. 6D illustrates a cross section of a tip of a dilator sensor device 630 with an unequal number of source structures and detector structures. In FIG. 6C, the sensor unit includes a single source structure S1 and two detector structures D1 and D2. In an implementation, the distance between source structure S1 and detector structure D1 is not equal to the distance between source structure S1 and detector structure D2.

While FIGS. 5A through 6D illustrate embodiments with two, three, or four sensor openings in the sensor unit, any suitable number of sensor openings can be present in the sensor unit. For example, there may be one, two, three, four, five, six, seven, or eight or more sensor openings. Any one or more sensor openings can be source structures, and any one or more sensor openings can be detector structures. A number of source structures can be equal to a number of detector structures in the sensor unit, or they can be different.

There are various other implementations of sensor opening patterns which can be incorporated into a sensor unit. Some of these implementations are discussed in U.S. Pat. No. 7,355,688, U.S. patent application Ser. No. 12/126,860, filed May 24, 2008, U.S. patent application Ser. No. 12/178,359, filed Jul. 23, 2008, and U.S. patent application Ser. No. 12/410,007, filed Mar. 24, 2009. These patent and patent applications are assigned to the same assignee as this patent application and are incorporated by reference.

Figure 7A:
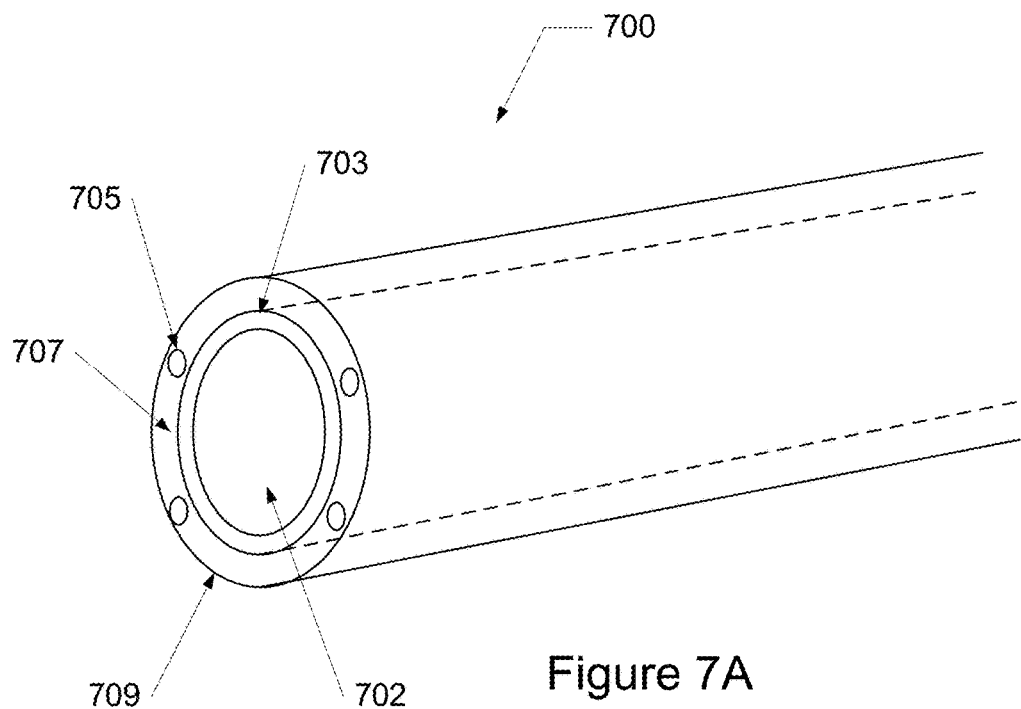
FIG. 7A shows a dilator sensor device with a dilator surrounded by a sensor probe.
Figure 7B:
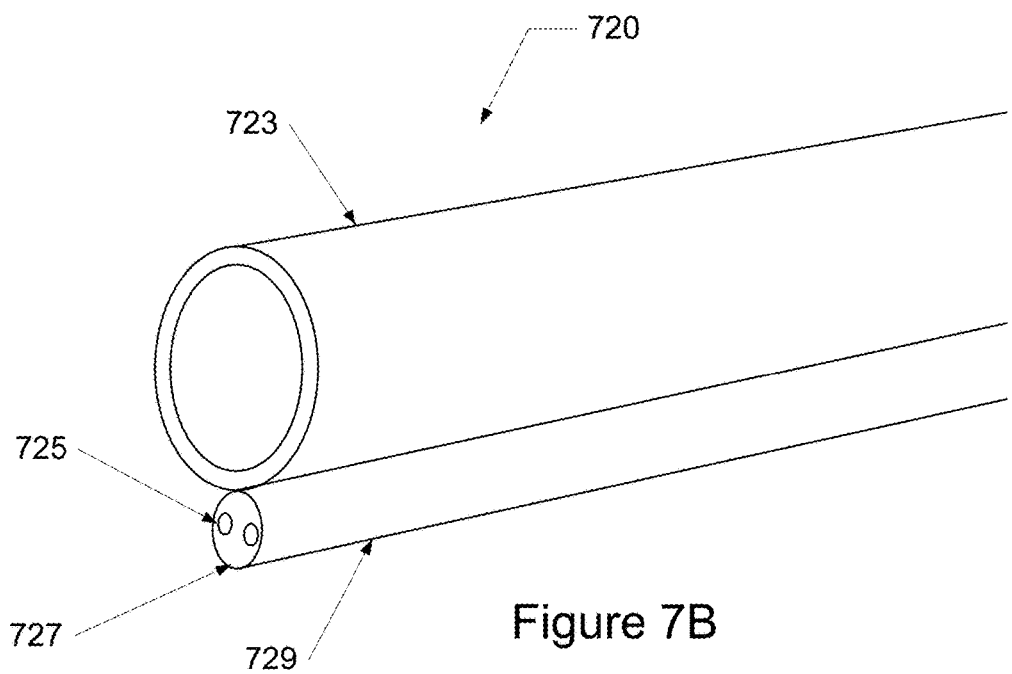
FIG. 7B shows a dilator sensor device with a dilator and a sensor probe which is attached to an outer surface of the dilator.

Although FIGS. 5A through 6D illustrate embodiments of the invention where a dilator sensor device includes optical fibers inside a dilator, optical fibers may be located elsewhere. FIGS. 7A and 7B illustrate embodiments in accordance with the present invention where optical fibers are not located inside the lumen of a dilator, but are coupled to an outer surface of the dilator.

FIG. 7A shows a dilator sensor device 700 that includes a dilator 703 with an axial lumen 702 and a sensor probe 709 which surrounds dilator 703. Sensor probe 709 includes four optical fibers 705 in a sheath material 707 which surrounds and holds the optical fibers in their positions. The sheath material may be any suitable biocompatible material such as silicone or polyurethane.

FIG. 7B shows another dilator sensor device 720 with a dilator 723 and a sensor probe which is axially aligned with and attached to an outer surface of the dilator. The sensor probe has two optical fibers 725 which are surrounded by a sheath material 727.

In the embodiments shown in FIGS. 7A and 7B, the lumen of the dilator is empty since a sensor probe is coupled to the dilator on the outer surface of the dilator. These embodiments may be particularly useful when it is desired to insert a surgical tool, such as a K-wire, through the lumen of the dilator.

When a dilator sensor device includes a series of sequential dilators as shown in FIG. 3A, a single sensor probe may be coupled to all the dilators in series. As shown in FIG. 3A, a single sensor probe may be threaded through the lumens of all the dilators in series. Alternatively, each dilator in the series may include its own sensor probe.

FIG. 7C illustrates another implementation of a dilator sensor device 730 where a scanning surface with sensor openings is located on a side wall of the dilator near its distal end region. FIG. 7D illustrates a longitudinal cross section of a tip region 731 of the dilator sensor device shown in FIG. 7C. Dilator sensor device 730 includes a dilator 735 and a sensor probe 736. The sensor probe includes a sensor unit 741 at the tip of the dilator which includes distal ends of optical fibers 743. A sensor unit or sensor head refers to a portion of a device (typically located at a distal end region of the device) which has sensor openings coupled with optical fibers and provides a scanning surface or surfaces to make optical measurements. The sensor probe also includes a connector 745 which contains proximal ends of the optical fibers, and a cable 749 which encases the optical fibers in a cable jacket. In FIG. 7C, the connector is disassociated to show proximal end portion of optical fibers 743.

In the implementation shown in FIGS. 7C and 7D, four sensor openings 751 of the dilator sensor device are located on a side wall of a distal end region of dilator 735, rather at the open end of the dilator at its tip as shown in FIGS. 4A and 4B. The dilator sensor device shown in FIGS. 7C and 7D may be referred to as a device with a side looking sensor array, whereas the dilator sensor device shown in FIGS. 4A and 4B may be referred to as a device with a forward looking sensor array. A dilator sensor device with a side looking sensor array can detect the presence of a blood vessel which may be located around the side wall of the dilator, whereas a dilator sensor device with a forward looking sensor array can detect the presence of a blood vessel which may be located in front of the tip of the dilator sensor device.

As shown in FIG. 7D, the distal ends of the optical fibers are coupled to the sensor openings on the side wall of the dilator. In this implementation, sensor unit 741 includes optical fibers 743a, 743b, 743c, and 743d which are threaded and inserted into four channels which are located on a side wall of dilator 735 near its tip. As shown in FIG. 7D, the distal ends of the optical fibers are flushed with the outer surface of the dilator side wall to provide a side looking sensor array. The optical fibers may be adhesively attached inside the dilator to prevent them from moving around. A cylindrical block 752 may be used to block the lumen of the dilator at its tip to prevent tissue debris from entering into the dilator sensor device during a surgical procedure.

In the implementation shown in FIGS. 7C and 7D, the sensor openings are arranged in a linear array. In one embodiment, the distal ends of optical fibers 743a and 743b may be source structures (S1 and S2, respectively) which transmit light from a light source into tissue, and the distal ends of optical fibers 743c and 743d may be detector structures (D1 and D2, respectively) which detect or collect light reflected from the tissue and transmit to a photodetector. If desired, the sensor openings may be aligned with a triangular marking 742 (which is also aligned with a longitudinal line 746 at a neck region 748) to assist a surgeon to determine the orientation of the sensor openings once the tip of the dilator sensor device is inside a patient.

In other implementations, sensor openings may be arranged in different configurations (e.g., a diamond, a rectangle, or a square for four sensor openings), and there may be more than four sensor openings or less than four sensor openings. For instance, a dilator sensor device may have multiple sets (e.g., three, four, five, or more) of sensor openings in a linear array all the way around the side wall at a distal end region of the dilator.

FIG. 7E illustrates another implementation of a dilator sensor device 760 having a sensor unit 762 which includes distal end portions of two sets of optical fibers—the first set which forms a forward looking sensor array and the second set which forms a side looking sensor array. The distal end regions of the first set of optical fibers 761 are aligned along the longitudinal axis of the dilator sensor device, and are inserted into channels of a cylindrical block 765. The cylindrical block may be attached to an inner wall of the dilator by an adhesive. The distal end portions of the second set of optical fibers 763 are inserted into channels on the side wall of dilator 767, and the distal ends of the optical fiber are flushed with the outer surface of the dilator side wall. If desired, an adhesive may be used to firmly attach the second set of optical fibers inside the lumen of the dilator sensor device. In this implementation, since the dilator sensor device includes both the forward looking sensor array and the side looking sensor array, the dilator sensor device can detect the presence of a blood vessel in front of the tip of the device as well as on the side of the device.

In a specific implementation, the optical fibers forming the forward looking sensor array are attached to a first channel (e.g., a receptacle) of the system unit, and the optical fibers forming the side looking sensor array are attached a second, independent channel (e.g., receptacle) of the system unit. The optical fibers forming the forward looking sensor array and the optical fibers forming the side looking sensor array may be directly attached to the first channel and second channel, respectively, of the system unit. Alternatively, the proximal end portions of the optical fibers forming the forward looking sensor array can be coupled to a connector, which then connects the optical fibers to the first channel of the system unit. Also, the proximal end portions of the optical fibers forming the side looking sensor array can be coupled to another connector, which then connects the optical fibers to the second channel of the system unit.

By using separate channels in the system unit, optical signals to and from the fibers of the forward looking sensor array can be controlled independently from optical signals to and from the fibers of the side looking sensor array. For example, the optical signals to and from the sensors connected to the first channel will not interfere with those on the second channel, and vice versa. Any signals transferred over the first channel will appear only at the sensors attached to the first channel or at the first channel input of the system unit. Any signals transferred over the second channel will appear only at the sensors attached to the second channel or at the first channel input of the system.

In another implementation, the proximal ends of both sets of optical fibers (i.e., forward looking sensor and side looking sensor) can be attached to a single connector, which can then be connected to a single channel of the system unit. It may be desirable to use a single connector for all of the optical fibers and attach the connector to a single channel of the system unit to reduce cost, if the total number of optical fibers included in a dilator sensor device is not too large (e.g., eight or less).

Dilator sensor devices in accordance with the present invention can be applied in a variety of minimally invasive surgeries. A dilator sensor device can be inserted into a body cavity towards a target location, while monitoring the presence of blood vessels along the way. A sensor unit in the dilator sensor device can transmit light into a body tissue as the device is gradually inserted towards the target location. Based on light reflected from the tissue, the monitoring console can calculate various parameters (e.g., a signal level of returned light, oxygen saturation level, hemoglobin concentration, blood flow, and pulse rate). Based on one or more of these parameters, a surgeon can determine if a blood vessel is in the pathway towards the target location. If it is determined that a blood vessel is near at the tip of a dilator sensor device, the tip of the dilator can be rerouted to avoid the blood vessel.

Figure 8:
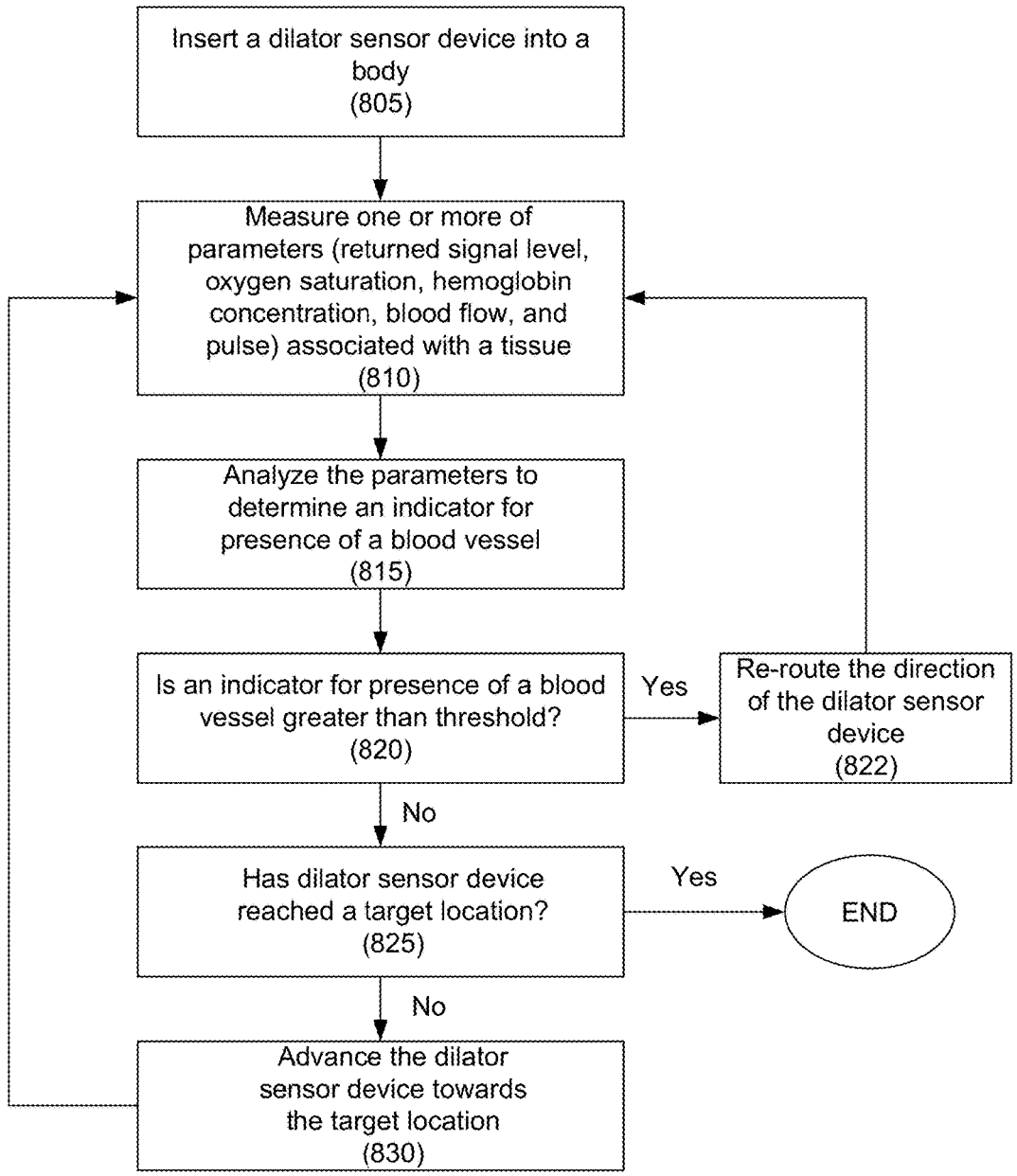
FIG. 8 shows a flowchart of advancing a dilator sensor device and obtaining optical measurements to reach a target location without rupturing a blood vessel.

FIG. 8 shows a flowchart for guiding a dilator sensor device to a target location based on an indicator or index for presence of a blood vessel determined by various physiological parameters of a tissue located at a tip of the dilator sensor device.

At step 805, a surgeon gradually and slowly inserts a dilator sensor device into a body through an incision. The tip of the dilator sensor device is directed towards a target surgical location.

At step 810, light is transmitted through optical fibers of the dilator sensor device through openings in the sensor unit located at the tip of the dilator sensor device. Light scatters in a tissue located at or nearby the tip of the dilator sensor device, and reflected light is detected by the sensor unit, which is returned to a monitoring console. Based on the initial light and the reflected light information, the console can measure and calculate various parameters associated with the tissue. These parameters include a signal level of returned light, an oxygen saturation level, a total hemoglobin concentration, a blood flow, and a pulse.

At step 815, the console analyzes one or more of measured parameters and determines an index or indicator for presence of a blood vessel at or nearby the tip of the dilator sensor device. The index may be based on whether each of the measured parameters meets its own threshold. Alternatively, the indicator or index may be based on whether a combination of one or more measured parameters meets a predetermined threshold as described above.

At step 820, if an indicator for presence of a blood vessel at or nearby the tip of the dilator sensor device is greater than a predetermined threshold, then the dilator sensor device may be rerouted towards a different direction in step 822. For example, the dilator sensor device may be moved backwards and then may be moved forward at a certain angle (e.g., 30 degrees) to avoid puncturing the blood vessel.

After step 822, at a new location, one or more parameters associated with a tissue at the new location are measured as described in step 810 and subsequent steps are repeated.

If the indicator for presence of a blood vessel at or nearby the tip of the dilator sensor device is less than a predetermined threshold in step 820, then it is determined whether the dilator sensor device has reached a target location in step 825. The dilator sensor device can be visualized inside the body using X-ray, ultrasound, or other visual aid techniques. Alternatively or additionally, when the tip of the dilator sensor device reaches its target location (e.g., disc), the surgeon can feel the change in density that is associated with the target surgical location. If it is determined that the dilator sensor device has reached the target surgical location, then this is the end of this portion of the surgery.

At step 825, if it is determined that the dilator sensor device has not reached its target surgical location, then the dilator sensor device is further advanced towards the target surgical location in step 830. At a new location, one or more parameters associated with a tissue at the new location are measured as described in step 810 and subsequent steps are repeated until the dilator sensor device reaches the target location.

While the steps shown in FIG. 8 are described as discrete steps of moving the dilator sensor device, the measurements of parameters are performed continuously while the dilator sensor device gradually moves along the pathway towards the target surgical location. As described above, some of the parameters may be measured every 0.5 seconds or so.

Figure 9:
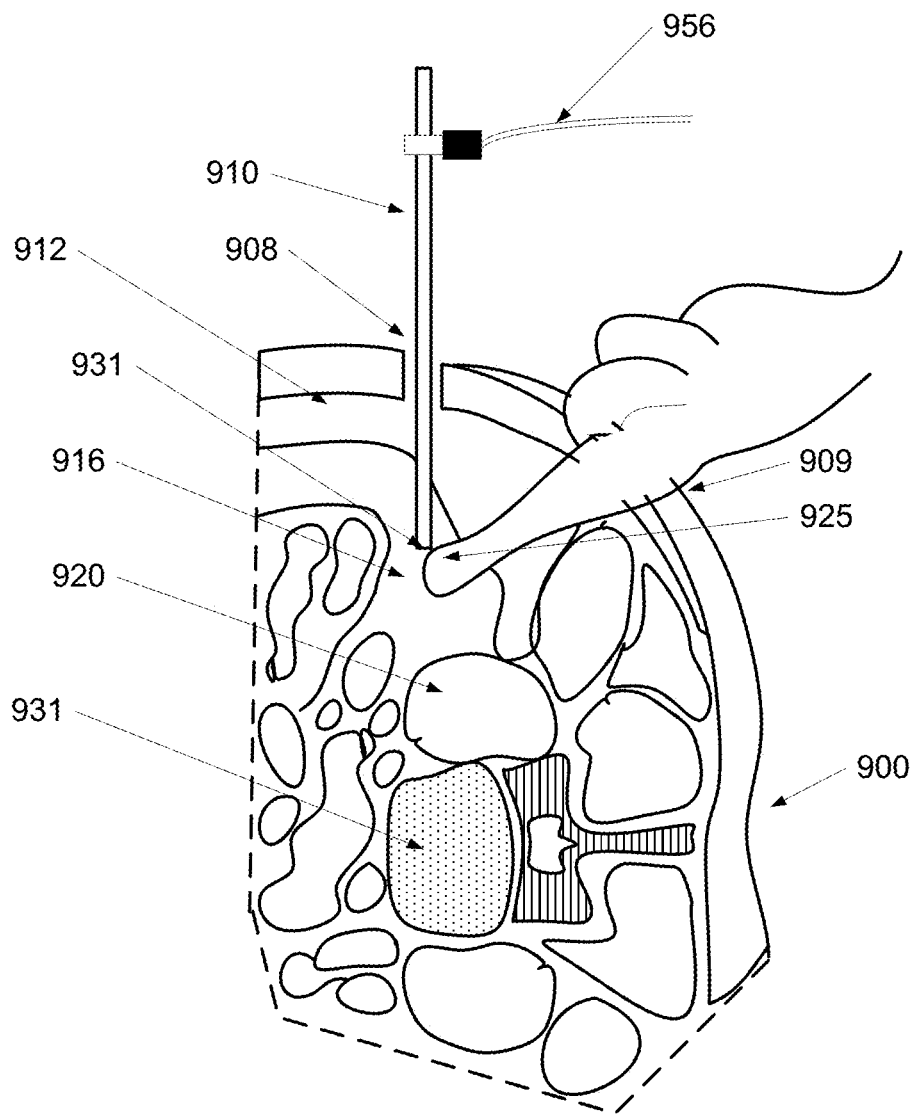
FIG. 9 shows a pictorial diagram of a minimally invasive lateral lumbar surgery where a finger is inserted to guide a dilator sensor device towards the lumbar region of the spine.
Figure 10:
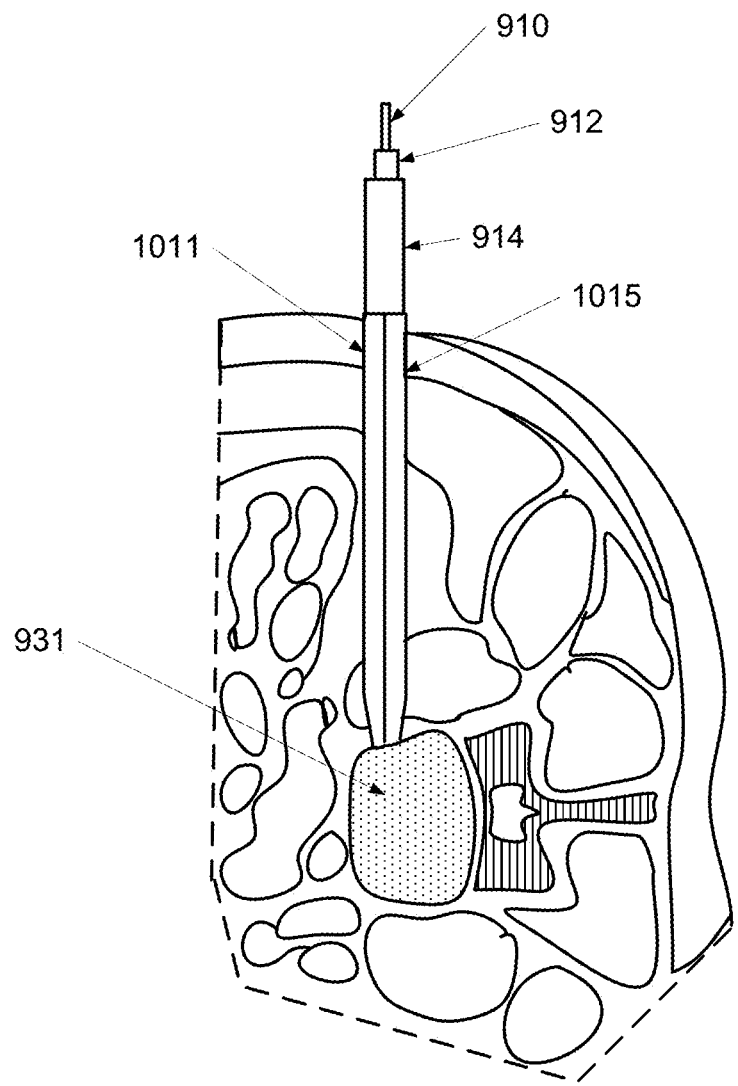
FIG. 10 shows a pictorial diagram of a minimally invasive lateral lumbar surgery where supplemental dilators and retractor blades are inserted over the initial dilator sensor device.

FIGS. 9 and 10 illustrate one implementation of the invention where a dilator sensor device is used in a minimally invasive lateral lumbar surgery. A minimally invasive lateral lumbar surgery is used to correct defects in the lumbar region of the spine. This technique uses a direct lateral, retroperitoneal approach to access the intervertebral disc with minimal disruption to the muscle and surrounding tissue. The technique utilizes a surgical access system such as a tissue distraction assembly and a tissue retraction assembly to establish an operative corridor to a surgical target site. The operative corridor is established through the retroperitoneal space and the psoas muscle during a direct lateral, retroperitoneal approach to the spine.

General discussions regarding a minimally invasive lateral lumbar surgery and a nerve monitoring system can be found in U.S. patent application publication US2005/0149035, published on Jul. 7, 2005; U.S. Pat. Nos. 7,207,949; 7,522,953; PCT application serial number PCT/US02/22247, filed on Jul. 11, 2002; PCT application serial number PCT/US02/30617 filed on Sep. 25, 2002; and PCT application serial number PCT/US02/35047, filed on Oct. 30, 2002; and PCT application serial number PCT/US03/02056, filed Jan. 15, 2003. All of these references (which are collectively referred to as lateral lumbar surgery references) are incorporated by reference in this application. The technique described in the references allows maximum surgical access to the lumbar region while minimizing the soft tissue damage during surgery. Furthermore, the technique allows direct visualization of the patient's anatomy through conventional methods without utilizing additional visualization tools such as those used in endoscopic surgeries.

FIG. 9 shows a cross section of a lumbar region of a patient lying down on his side, and penetration of an initial dilator 910 into a surgical target site 931 via a lateral, retroperitoneal approach to the spine of the patient. Prior to inserting the initial dilator, an incision is made on the patient at a posteriolateral incision location 909 near the lateral incision location 908 where the initial dilator 910 is to be inserted. The subcutaneous layers are dissected until reaching muscular mass 912. A blunt dissection tool (e.g., a blunt dissection scissors) is used to spread muscle fibers 912 until the retroperitoneal space 916 is reached.

A guider 925 (e.g., a finger of a surgeon) is inserted through incision 909 into the retroperitoneal space 916 to identify the psoas muscle 920. After identifying the psoas muscle 920 with the finger, the surgeon redirects his finger inside the peritoneal space towards the lateral incision location 908. Another incision 908 is made so that a distal end 931 of the initial dilator can be introduced into the peritoneal cavity. The finger 925 reaches the distal end of the initial dilator and guides the dilator through the retroperitoneal space towards the psoas muscle 920.

While the dilator advances inside the body, the monitoring system in accordance with the present invention may transmit optical signals and receive reflected signals from the tissue to determine whether the tip of the dilator is touching or nearby a blood vessel. When the monitoring system determines that there is a blood vessel nearby or at the tip of the dilator, the dilator can be pulled backwards and rerouted around the blood vessel to reach the target location.

In a specific implementation, a nerve monitoring system can be used in addition to a blood vessel monitoring system. Descending nerves of the lumbar plexus typically lie in the posterior one-third of the psoas muscle 920. A nerve monitoring system described in the lateral lumbar surgery references cited above can be used to monitor the presence of a nerve nearby or at the tip of the dilator so that the dilator can be safely pass through the psoas muscle towards a surgical target site.

Briefly, the nerve monitoring system in the cited references utilizes evoked-EMG monitoring to determine proximity of a nerve from the tip of the dilator. A stimulation connector 956 of the nerve monitoring system is connected to a proximal end region of the dilator. The nerve monitoring system transmits a stimulation signal as the dilator 910 is advanced through the psoas muscle. The nerve monitoring system searches for the stimulus threshold that elicits an EMG response on the myotomes. The stimulus thresholds can be visually and audibly presented to the surgeon.

The stimulus necessary to elicit an EMG response depends on the distance of the tip of the dilator (where an electrode is located) and the nerve. When the stimulus source (i.e., the tip of the dilator) is closer to the nerve, the less stimulus intensity is required to elicit a response and thus the stimulus threshold is lower. Typically, threshold values greater than 10 mA indicate a distance that allows for safe passage of the dilator sensor device through the psoas muscle without damaging the nerve.

Any suitable nerve monitoring system may be used to determine proximity of a nerve from the tip of the dilator sensor device. In one implementation, the monitoring system for blood vessel avoidance in accordance the invention can be integrated into a nerve monitoring system (e.g., in a single housing). In another implementation, the monitoring system for blood vessel avoidance may communicate with a nerve monitoring system via USB connection, wireless communication, or others.

FIG. 10 illustrates that one or more supplemental dilators 912 and 914 may be guided over the initial dilator 910 to further dilate the tissue down to the surgical target site 931. The monitoring system in accordance with the present invention can be used to determine the presence of blood vessels near the tips of the supplemental dilators. In addition, a nerve monitoring system may also be used concurrently to determine if there is a nerve in the pathway of the supplemental dilators. As shown in FIG. 10, retractor blades 1011 and 1015 are introduced over the supplemental dilator 914 to establish a surgical corridor. Mechanics and structures of the retractor blades and other surgical tools are further described in detail in U.S. patent application publication 2005/0149035A1 and other lateral lumbar surgery references cited above.

While the dilator sensor devices and systems are described above, the above discussions can be applied to any penetration instruments. For example, instead of a dilator, a sensor probe can be coupled to a hollow needle instrument or a trocar. Examples of a hollow needle instrument include a biopsy needle, core biopsy needle, phlebotomy needle, intravenous catheter needle, spinal tap needle, Verres needle, and others.

Furthermore, while the use of the penetration sensor devices and systems is discussed in the context of avoiding a blood vessel when a device is advanced through a body towards a target surgical location, the penetration sensor devices and systems can also be used in finding a blood vessel for the purpose of penetrating the blood vessel.

For example, when drawing blood from a patient, it may be difficult to find a blood vessel for some patients. A phlebotomy needle can be coupled with a sensor probe in accordance with the present invention to find a blood vessel in a patient. In another example, it may be desirable to locate a coronary artery which may be diseased and needs to be operated. A penetration sensor device and system in accordance with the present invention can be used to locate the coronary artery.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method comprising:
   providing a penetration sensor device comprising a tip and a sensor probe, wherein the sensor probe comprises a sensor unit comprising an emitter sensor opening and a detector sensor opening;
   from a signal emitter component, transmitting a first light signal through the emitter sensor opening in a direction ahead of the tip into a tissue;
   from a signal detector component, receiving a second light signal reflected from the tissue ahead of the tip through the detector sensor opening of the penetration sensor device;
   based on information from the first light signal and the second light signal, determining an indication of presence of a blood vessel ahead of the tip of the penetration sensor device; and
   identifying the tissue as a blood vessel if the indication for presence of a blood vessel is greater than a threshold, thereby differentiating a blood vessel from a nonvascular tissue inside a patient's body cavity during a surgical procedure.

2. The method of claim 1 wherein the indication for presence of a blood vessel is determined based on one or combinations of parameters which include a signal level of the second light, a total hemoglobin concentration, an oxygen saturation level, a blood flow, and a pulse.

3. The method of claim 1 wherein the penetration sensor device comprises a dilator sensor device.

4. The method of claim 1 comprising:
   alerting a user if the indication for presence of a blood vessel indicates that there is a blood vessel at or nearby the tip of the sensor probe.

5. The method of claim 1 comprising:
   using a notification component to instruct a user to advance the penetration sensor device towards a target location if the indication for presence of a blood vessel indicates that the tip of the sensor probe is touching a nonvascular tissue.

6. The method of claim 1 comprising:
   using a notification component to instruct a user to reroute the penetration sensor device into a different direction if the indication for presence of a blood vessel indicates that the tip of the sensor probe is nearby or touching a blood vessel so that the blood vessel is not punctured by the penetration sensor device.

7. The method of claim 1 wherein the penetration sensor device comprises at least one of a dilator sensor device, a needle sensor device, or a trocar sensor device.

8. The method of claim 1 wherein the penetration sensor device comprises a first optical fiber coupled to the emitter sensor opening and a second optical fiber coupled to the detector sensor opening.

9. The method of claim 1 wherein the emitter sensor opening is positioned on the sensor unit, and the detector sensor opening is positioned on the sensor unit.

10. A method comprising:
    providing a penetration sensor system comprising a tip and a sensor probe, wherein the sensor probe comprises a sensor unit comprising an emitter sensor opening and a detector sensor opening;

using a signal emitter circuit of the system to transmit a first light signal through the emitter sensor opening in a direction ahead of the tip into a tissue;
using a signal detector circuit of the system to receive a second light signal reflected from the tissue ahead of the tip through a detector sensor opening of the penetration sensor device; and
using an analysis circuit of the system to determine an indication of presence of a blood vessel ahead of the tip of the penetration sensor device based on information from the first light signal and the second light signal, and identify the tissue as a blood vessel if the indication for presence of a blood vessel is greater than a threshold, thereby differentiating a blood vessel from a nonvascular tissue inside a patient's body cavity during a surgical procedure.

11. The method of claim 10 wherein the indication for presence of a blood vessel is determined based on one or combinations of parameters which include a signal level of the second light, a total hemoglobin concentration, an oxygen saturation level, a blood flow, and a pulse.

12. The method of claim 10 wherein the penetration sensor system comprises a dilator sensor device.

13. The method of claim 10 comprising:
using a notification component of the system to alert a user if the indication for presence of a blood vessel indicates that there is a blood vessel at or nearby the tip of the sensor probe.

14. The method of claim 10 comprising:
on a display of the system, showing an alert to a user to advance the penetration sensor device towards a target location if the indication for presence of a blood vessel indicates that the tip of the sensor probe is touching a nonvascular tissue.

15. The method of claim 10 comprising:
using a notification component to instruct a user to reroute the penetration sensor device into a different direction if the indication for presence of a blood vessel indicates that the tip of the sensor probe is nearby or touching a blood vessel so that the blood vessel is not punctured by the penetration sensor device.

16. The method of claim 10 wherein the penetration sensor system comprises at least one of a dilator sensor device, a needle sensor device, or a trocar sensor device.

17. The method of claim 10 wherein the penetration sensor system comprises a first optical fiber coupled to the emitter sensor opening and a second optical fiber coupled to the detector sensor opening.

18. The method of claim 10 wherein the emitter sensor opening is positioned on the sensor unit, and the detector sensor opening is positioned on the sensor unit.

19. A method comprising:
providing a penetration sensor device comprising a tip and a sensor probe, wherein the sensor probe comprises a sensor unit comprising an emitter sensor opening and a detector sensor opening;
from a light emitting diode, transmitting a first light signal through the emitter sensor opening in a direction ahead of the tip into a tissue;
from a photodetector, receiving a second light signal reflected from the tissue ahead of the tip through the detector sensor opening of the penetration sensor device;
based on information from the first light signal and the second light signal, determining an indication of presence of a blood vessel ahead of the tip of the penetration sensor device; and
identifying the tissue as a blood vessel if the indication for presence of a blood vessel is greater than a threshold, thereby differentiating a blood vessel from a nonvascular tissue inside a patient's body cavity during a surgical procedure.

20. The method of claim 19 wherein the indication for presence of a blood vessel is determined based on one or combinations of parameters which include a signal level of the second light, a total hemoglobin concentration, an oxygen saturation level, a blood flow, and a pulse.

21. The method of claim 19 wherein the penetration sensor device comprises a dilator sensor device.

22. The method of claim 19 comprising:
alerting a user if the indication for presence of a blood vessel indicates that there is a blood vessel at or nearby the tip of the sensor probe.

23. The method of claim 19 comprising:
using at least one of a speaker, light, or display to instruct a user to advance the penetration sensor device towards a target location if the indication for presence of a blood vessel indicates that the tip of the sensor probe is touching a nonvascular tissue.

24. The method of claim 19 comprising:
using at least one of a speaker, light, or display to instruct a user to reroute the penetration sensor device into a different direction if the indication for presence of a blood vessel indicates that the tip of the sensor probe is nearby or touching a blood vessel so that the blood vessel is not punctured by the penetration sensor device.

25. The method of claim 19 wherein the penetration sensor device comprises at least one of a dilator sensor device, a needle sensor device, or a trocar sensor device.

26. The method of claim 19 wherein the penetration sensor device comprises a first optical fiber coupled to the emitter sensor opening and a second optical fiber coupled to the detector sensor opening.

27. The method of claim 19 wherein the emitter sensor opening is positioned on the sensor unit, and the detector sensor opening is positioned on the sensor unit.

28. A method comprising:
providing a penetration sensor system comprising a tip and a sensor probe, wherein the sensor probe comprises a sensor unit comprising an emitter sensor opening and detector sensor opening;
using a light emitting diode of the system to transmit a first light signal through the emitter sensor opening in a direction ahead of the tip into a tissue;
using a photodetector of the system to receive a second light signal reflected from the tissue ahead of the tip through a detector sensor opening of the penetration sensor device; and
using a processor of the system to determine an indication of presence of a blood vessel ahead of the tip of the penetration sensor device based on information from the first light signal and the second light signal, and identify the tissue as a blood vessel if the indication for presence of a blood vessel is greater than a threshold, thereby differentiating a blood vessel from a nonvascular tissue inside a patient's body cavity during a surgical procedure.

29. The method of claim 28 wherein the indication for presence of a blood vessel is determined based on one or combinations of parameters which include a signal level of the second light, a total hemoglobin concentration, an oxygen saturation level, a blood flow, and a pulse.

30. The method of claim 28 wherein the penetration sensor system comprises a dilator sensor device.

31. The method of claim 28 comprising:
using at least one of a speaker, light, or display of the system to alert a user if the indication for presence of a blood vessel indicates that there is a blood vessel at or nearby the tip of the sensor probe.

32. The method of claim 28 comprising:
on a display of the system, showing an alert to a user to advance the penetration sensor device towards a target location if the indication for presence of a blood vessel indicates that the tip of the sensor probe is touching a nonvascular tissue.

33. The method of claim 28 comprising:
using at least one of a speaker, light, or display to instruct a user to reroute the penetration sensor device into a different direction if the indication for presence of a blood vessel indicates that the tip of the sensor probe is nearby or touching a blood vessel so that the blood vessel is not punctured by the penetration sensor device.

34. The method of claim 28 wherein the penetration sensor system comprises at least one of a dilator sensor device, a needle sensor device, or a trocar sensor device.

35. The method of claim 28 wherein the penetration sensor system comprises a first optical fiber coupled to the emitter sensor opening and a second optical fiber coupled to the detector sensor opening.

36. The method of claim 28 wherein the emitter sensor opening is positioned on the sensor unit, and the detector sensor opening is positioned on the sensor unit.

* * * * *